(12) United States Patent
Crawford et al.

(10) Patent No.: US 12,251,140 B2
(45) Date of Patent: *Mar. 18, 2025

(54) METHODS FOR PERFORMING MEDICAL PROCEDURES USING A SURGICAL ROBOT

(71) Applicant: GLOBUS MEDICAL, INC., Audubon, PA (US)

(72) Inventors: Neil Crawford, Chandler, AZ (US); Nicholas Theodore, Ruxton, MD (US)

(73) Assignee: Globus Medical, Inc., Audubon, PA (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/319,775

(22) Filed: May 18, 2023

(65) Prior Publication Data

US 2023/0285093 A1 Sep. 14, 2023

Related U.S. Application Data

(63) Continuation of application No. 16/708,545, filed on Dec. 10, 2019, now Pat. No. 11,690,687, which is a
(Continued)

(51) Int. Cl.
*A61B 34/30* (2016.01)
*A61B 5/06* (2006.01)
(Continued)

(52) U.S. Cl.
CPC .......... *A61B 17/7074* (2013.01); *A61B 5/061* (2013.01); *A61B 5/062* (2013.01);
(Continued)

(58) Field of Classification Search
CPC ..... A61B 19/2203; A61B 34/00; A61B 34/20; A61B 2034/107; A61B 2034/2055
See application file for complete search history.

(56) References Cited

U.S. PATENT DOCUMENTS

| 4,150,293 A | 4/1979 | Franke |
| 5,246,010 A | 9/1993 | Gazzara et al. |
(Continued)

FOREIGN PATENT DOCUMENTS

| EP | 0744633 A2 | 11/1996 |
| EP | 2286729 A2 | 2/2011 |
(Continued)

OTHER PUBLICATIONS

US 8,231,638 B2, 07/2012, Swarup et al. (withdrawn)
(Continued)

*Primary Examiner* — Julian W Woo

(57) ABSTRACT

Embodiments are directed to a medical robot system including a robot coupled to an end-effectuator element with the robot configured to control movement and positioning of the end-effectuator in relation to the patient. One embodiment is a method for removing bone with a robot system comprising: taking a two-dimensional slice through a computed tomography scan volume of target anatomy; placing a perimeter on a pathway to the target anatomy; and controlling a drill assembly with the robot system to remove bone along the pathway in the intersection of the perimeter and the two-dimensional slice.

13 Claims, 17 Drawing Sheets

Related U.S. Application Data continuation of application No. 14/476,101, filed on Sep. 3, 2014, now Pat. No. 10,531,927, which is a continuation of application No. 14/475,998, filed on Sep. 3, 2014, now abandoned, which is a continuation-in-part of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.
| | |
|---|---|
| *A61B 10/02* | (2006.01) |
| *A61B 17/02* | (2006.01) |
| *A61B 17/16* | (2006.01) |
| *A61B 17/17* | (2006.01) |
| *A61B 17/70* | (2006.01) |
| *A61B 17/88* | (2006.01) |
| *A61B 34/00* | (2016.01) |
| *A61B 34/10* | (2016.01) |
| *A61B 34/20* | (2016.01) |
| *A61B 34/32* | (2016.01) |
| *A61B 46/20* | (2016.01) |
| *A61B 50/13* | (2016.01) |
| *A61B 90/00* | (2016.01) |
| *A61B 90/14* | (2016.01) |
| *A61B 90/96* | (2016.01) |
| *A61B 90/98* | (2016.01) |
| *A61M 5/172* | (2006.01) |
| *A61N 1/05* | (2006.01) |
| *B25J 9/10* | (2006.01) |
| *A61B 17/00* | (2006.01) |
| *A61B 90/11* | (2016.01) |

(52) U.S. Cl.
CPC ............ *A61B 5/066* (2013.01); *A61B 10/02* (2013.01); *A61B 10/0233* (2013.01); *A61B 10/0275* (2013.01); *A61B 17/025* (2013.01); *A61B 17/1615* (2013.01); *A61B 17/1671* (2013.01); *A61B 17/1703* (2013.01); *A61B 17/1757* (2013.01); *A61B 17/7002* (2013.01); *A61B 17/7082* (2013.01); *A61B 17/8866* (2013.01); *A61B 34/10* (2016.02); *A61B 34/20* (2016.02); *A61B 34/25* (2016.02); *A61B 34/30* (2016.02); *A61B 34/32* (2016.02); *A61B 34/70* (2016.02); *A61B 34/74* (2016.02); *A61B 34/76* (2016.02); *A61B 46/20* (2016.02); *A61B 50/13* (2016.02); *A61B 90/37* (2016.02); *A61B 90/39* (2016.02); *A61B 90/96* (2016.02); *A61B 90/98* (2016.02); *A61M 5/172* (2013.01); *A61N 1/0529* (2013.01); *B25J 9/1065* (2013.01); *A61B 5/064* (2013.01); *A61B 2010/0208* (2013.01); *A61B 2017/00119* (2013.01); *A61B 2017/00203* (2013.01); *A61B 2017/00207* (2013.01); *A61B 2017/00876* (2013.01); *A61B 2017/0256* (2013.01); *A61B 17/17* (2013.01); *A61B 2034/107* (2016.02); *A61B 2034/2051* (2016.02); *A61B 2034/2055* (2016.02); *A61B 2034/2072* (2016.02); *A61B 2034/301* (2016.02); *A61B 2034/741* (2016.02); *A61B 2034/742* (2016.02); *A61B 2034/743* (2016.02); *A61B 2034/744* (2016.02); *A61B 2090/034* (2016.02); *A61B 2090/064* (2016.02); *A61B 2090/0811* (2016.02); *A61B 90/11* (2016.02); *A61B 90/14* (2016.02); *A61B 2090/365* (2016.02); *A61B 2090/374* (2016.02); *A61B 2090/3762* (2016.02); *A61B 2090/3764* (2016.02); *A61B 2090/378* (2016.02); *A61B 2090/3937* (2016.02); *A61B 2090/3941* (2016.02); *A61B 2090/3945* (2016.02); *A61B 2090/395* (2016.02); *A61B 2090/3966* (2016.02); *A61B 2090/3975* (2016.02); *A61B 2090/3979* (2016.02); *A61B 2090/3983* (2016.02)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,276,471 B1 | 8/2001 | Kratzenberg et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |

(56) References Cited

U.S. PATENT DOCUMENTS

| | | | |
|---|---|---|---|
| 6,711,431 B2 | 3/2004 | Sarin et al. | |
| 6,725,080 B2 * | 4/2004 | Melkent | A61B 6/5235 |
| | | | 606/130 |
| 6,757,068 B2 | 6/2004 | Foxlin | |
| 6,782,287 B2 | 8/2004 | Grzeszczuk et al. | |
| 6,783,524 B2 | 8/2004 | Anderson et al. | |
| 6,786,896 B1 | 9/2004 | Madhani et al. | |
| 6,788,018 B1 | 9/2004 | Blumenkranz | |
| 6,804,581 B2 | 10/2004 | Wang et al. | |
| 6,823,207 B1 | 11/2004 | Jensen et al. | |
| 6,827,351 B2 | 12/2004 | Graziani et al. | |
| 6,837,892 B2 | 1/2005 | Shoham | |
| 6,839,612 B2 | 1/2005 | Sanchez et al. | |
| 6,856,826 B2 | 2/2005 | Seeley et al. | |
| 6,856,827 B2 | 2/2005 | Seeley et al. | |
| 6,879,880 B2 | 4/2005 | Nowlin et al. | |
| 6,892,090 B2 | 5/2005 | Verard et al. | |
| 6,920,347 B2 | 7/2005 | Simon et al. | |
| 6,922,632 B2 | 7/2005 | Foxlin | |
| 6,968,224 B2 | 11/2005 | Kessman et al. | |
| 6,978,166 B2 | 12/2005 | Foley et al. | |
| 6,988,009 B2 | 1/2006 | Grimm et al. | |
| 6,991,627 B2 | 1/2006 | Madhani et al. | |
| 6,996,487 B2 | 2/2006 | Jutras et al. | |
| 6,999,852 B2 | 2/2006 | Green | |
| 7,007,699 B2 | 3/2006 | Martinelli et al. | |
| 7,016,457 B1 | 3/2006 | Senzig et al. | |
| 7,043,961 B2 | 5/2006 | Pandey et al. | |
| 7,062,006 B1 | 6/2006 | Pelc et al. | |
| 7,063,705 B2 | 6/2006 | Young et al. | |
| 7,072,707 B2 | 7/2006 | Galloway, Jr. et al. | |
| 7,083,615 B2 | 8/2006 | Peterson et al. | |
| 7,097,640 B2 | 8/2006 | Wang et al. | |
| 7,099,428 B2 | 8/2006 | Clinthorne et al. | |
| 7,108,421 B2 | 9/2006 | Gregerson et al. | |
| 7,130,676 B2 | 10/2006 | Barrick | |
| 7,139,418 B2 | 11/2006 | Abovitz et al. | |
| 7,139,601 B2 | 11/2006 | Bucholz et al. | |
| 7,155,316 B2 | 12/2006 | Sutherland et al. | |
| 7,164,968 B2 | 1/2007 | Treat et al. | |
| 7,167,738 B2 | 1/2007 | Schweikard et al. | |
| 7,169,141 B2 | 1/2007 | Brock et al. | |
| 7,172,627 B2 | 2/2007 | Fiere et al. | |
| 7,194,120 B2 | 3/2007 | Wicker et al. | |
| 7,197,107 B2 | 3/2007 | Arai et al. | |
| 7,231,014 B2 | 6/2007 | Levy | |
| 7,231,063 B2 | 6/2007 | Naimark et al. | |
| 7,239,940 B2 | 7/2007 | Wang et al. | |
| 7,248,914 B2 | 7/2007 | Hastings et al. | |
| 7,301,648 B2 | 11/2007 | Foxlin | |
| 7,302,288 B1 | 11/2007 | Schellenberg | |
| 7,313,430 B2 | 12/2007 | Urquhart et al. | |
| 7,318,805 B2 | 1/2008 | Schweikard et al. | |
| 7,318,827 B2 | 1/2008 | Leitner et al. | |
| 7,319,897 B2 | 1/2008 | Leitner et al. | |
| 7,324,623 B2 | 1/2008 | Heuscher et al. | |
| 7,327,865 B2 | 2/2008 | Fu et al. | |
| 7,331,967 B2 | 2/2008 | Lee et al. | |
| 7,333,642 B2 | 2/2008 | Green | |
| 7,339,341 B2 | 3/2008 | Oleynikov et al. | |
| 7,366,562 B2 | 4/2008 | Dukesherer et al. | |
| 7,379,790 B2 | 5/2008 | Toth et al. | |
| 7,386,365 B2 | 6/2008 | Nixon | |
| 7,422,592 B2 | 9/2008 | Morley et al. | |
| 7,435,216 B2 | 10/2008 | Kwon et al. | |
| 7,440,793 B2 | 10/2008 | Chauhan et al. | |
| 7,460,637 B2 | 12/2008 | Clinthorne et al. | |
| 7,466,303 B2 | 12/2008 | Yi et al. | |
| 7,493,153 B2 | 2/2009 | Ahmed et al. | |
| 7,505,617 B2 | 3/2009 | Fu et al. | |
| 7,533,892 B2 | 5/2009 | Schena et al. | |
| 7,542,791 B2 | 6/2009 | Mire et al. | |
| 7,555,331 B2 | 6/2009 | Viswanathan | |
| 7,567,834 B2 | 7/2009 | Clayton et al. | |
| 7,594,912 B2 | 9/2009 | Cooper et al. | |
| 7,606,613 B2 | 10/2009 | Simon et al. | |
| 7,607,440 B2 | 10/2009 | Coste-Maniere et al. | |
| 7,623,902 B2 | 11/2009 | Pacheco | |
| 7,630,752 B2 | 12/2009 | Viswanathan | |
| 7,630,753 B2 | 12/2009 | Simon et al. | |
| 7,643,862 B2 | 1/2010 | Schoenefeld | |
| 7,660,623 B2 | 2/2010 | Hunter et al. | |
| 7,661,881 B2 | 2/2010 | Gregerson et al. | |
| 7,683,331 B2 | 3/2010 | Chang | |
| 7,683,332 B2 | 3/2010 | Chang | |
| 7,689,320 B2 | 3/2010 | Prisco et al. | |
| 7,691,098 B2 | 4/2010 | Wallace et al. | |
| 7,702,379 B2 | 4/2010 | Avinash et al. | |
| 7,702,477 B2 | 4/2010 | Tuemmler et al. | |
| 7,711,083 B2 | 5/2010 | Heigl et al. | |
| 7,711,406 B2 | 5/2010 | Kuhn et al. | |
| 7,720,523 B2 | 5/2010 | Omernick et al. | |
| 7,725,253 B2 | 5/2010 | Foxlin | |
| 7,726,171 B2 | 6/2010 | Langlotz et al. | |
| 7,742,801 B2 | 6/2010 | Neubauer et al. | |
| 7,751,865 B2 | 7/2010 | Jascob et al. | |
| 7,760,849 B2 | 7/2010 | Zhang | |
| 7,762,825 B2 | 7/2010 | Burbank et al. | |
| 7,763,015 B2 | 7/2010 | Cooper et al. | |
| 7,787,699 B2 | 8/2010 | Mahesh et al. | |
| 7,796,728 B2 | 9/2010 | Bergfjord | |
| 7,813,838 B2 | 10/2010 | Sommer | |
| 7,818,044 B2 | 10/2010 | Dukesherer et al. | |
| 7,819,859 B2 | 10/2010 | Prisco et al. | |
| 7,824,401 B2 | 11/2010 | Manzo et al. | |
| 7,831,294 B2 | 11/2010 | Viswanathan | |
| 7,834,484 B2 | 11/2010 | Sartor | |
| 7,835,557 B2 | 11/2010 | Kendrick et al. | |
| 7,835,778 B2 | 11/2010 | Foley et al. | |
| 7,835,784 B2 | 11/2010 | Mire et al. | |
| 7,840,253 B2 | 11/2010 | Tremblay et al. | |
| 7,840,256 B2 | 11/2010 | Lakin et al. | |
| 7,843,158 B2 | 11/2010 | Prisco | |
| 7,844,320 B2 | 11/2010 | Shahidi | |
| 7,853,305 B2 | 12/2010 | Simon et al. | |
| 7,853,313 B2 | 12/2010 | Thompson | |
| 7,865,269 B2 | 1/2011 | Prisco et al. | |
| D631,966 S | 2/2011 | Perloff et al. | |
| 7,879,045 B2 | 2/2011 | Gielen et al. | |
| 7,881,767 B2 | 2/2011 | Strommer et al. | |
| 7,881,770 B2 | 2/2011 | Melkent et al. | |
| 7,886,743 B2 | 2/2011 | Cooper et al. | |
| RE42,194 E | 3/2011 | Foley et al. | |
| RE42,226 E | 3/2011 | Foley et al. | |
| 7,900,524 B2 | 3/2011 | Calloway et al. | |
| 7,907,166 B2 | 3/2011 | Lamprecht et al. | |
| 7,909,122 B2 | 3/2011 | Schena et al. | |
| 7,925,653 B2 | 4/2011 | Saptharishi | |
| 7,930,065 B2 | 4/2011 | Arkin et al. | |
| 7,935,130 B2 | 5/2011 | Williams | |
| 7,940,999 B2 | 5/2011 | Liao et al. | |
| 7,945,012 B2 | 5/2011 | Ye et al. | |
| 7,945,021 B2 | 5/2011 | Shapiro et al. | |
| 7,953,470 B2 | 5/2011 | Vetter et al. | |
| 7,954,397 B2 | 6/2011 | Choi et al. | |
| 7,971,341 B2 | 7/2011 | Dukesherer et al. | |
| 7,974,674 B2 | 7/2011 | Hauck et al. | |
| 7,974,677 B2 | 7/2011 | Mire et al. | |
| 7,974,681 B2 | 7/2011 | Wallace et al. | |
| 7,979,157 B2 | 7/2011 | Anvari | |
| 7,983,733 B2 | 7/2011 | Viswanathan | |
| 7,988,215 B2 | 8/2011 | Seibold | |
| 7,996,110 B2 | 8/2011 | Lipow et al. | |
| 8,004,121 B2 | 8/2011 | Sartor | |
| 8,004,229 B2 | 8/2011 | Nowlin et al. | |
| 8,010,177 B2 | 8/2011 | Csavoy et al. | |
| 8,019,045 B2 | 9/2011 | Kato | |
| 8,021,310 B2 | 9/2011 | Sanborn et al. | |
| 8,035,685 B2 | 10/2011 | Jensen | |
| 8,046,054 B2 | 10/2011 | Kim et al. | |
| 8,046,057 B2 | 10/2011 | Clarke | |
| 8,052,688 B2 | 11/2011 | Wolf, II | |
| 8,054,184 B2 | 11/2011 | Cline et al. | |
| 8,054,752 B2 | 11/2011 | Druke et al. | |

(56) References Cited

U.S. PATENT DOCUMENTS

| | | |
|---|---|---|
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |

(56) References Cited

U.S. PATENT DOCUMENTS

| | | |
|---|---|---|
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,782,229 B2 * | 10/2017 | Crawford ............ A61B 10/0233 |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,531,927 B2 * | 1/2020 | Crawford ............ A61N 1/0529 |
| 11,690,687 B2 * | 7/2023 | Crawford ............ A61B 17/7082 606/130 |
| 2001/0036302 A1 | 11/2001 | Miller |
| 2002/0035321 A1 | 3/2002 | Bucholz et al. |
| 2003/0055049 A1 | 3/2003 | Brock |
| 2003/0153829 A1 | 8/2003 | Sarin et al. |
| 2004/0024311 A1 | 2/2004 | Quaid |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2005/0245820 A1 | 11/2005 | Sarin |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |

(56) References Cited

U.S. PATENT DOCUMENTS

| | | |
|---|---|---|
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0066944 A1 | 3/2014 | Taylor et al. |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2014/0379130 A1 | 12/2014 | Lee et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |

(56) References Cited

U.S. PATENT DOCUMENTS

| | | |
|---|---|---|
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| JP | 898843 A | 4/1996 |
| JP | 8313304 A | 11/1996 |
| JP | 2008538184 A | 10/2008 |
| WO | 02071369 A1 | 9/2002 |
| WO | 2012018816 A3 | 2/2012 |

OTHER PUBLICATIONS

Edward Ramsden, Hall Effect Sensors; Theory and Application (2nd Edition), pp. 107-130, http://store.elsevier.com/Hall-Effect-Sensors/Edward-Ramsden/isbn-9780080523743/. Feb. 28, 2006.

Shuanghui, Hao et al., Study on a novel absolute magnetic encoder, Robotice and Biomemetics, 2009, ROBIO, 2009. IEEE, International Conference On IEEE. pp. 1773-1776, Feb. 22, 2009.

Eric M. Yeatmann et al., "Use of Scanned Detection in Optical Position Encoders", IEEE, Transactions of Instrumentation and Measurement. vol. 53, No. 1, pp. 37-44. http://www3.imperial.ac.uk/pls/portallive/docs/1/375913.PDF. Feb. 28, 2004.

\* cited by examiner

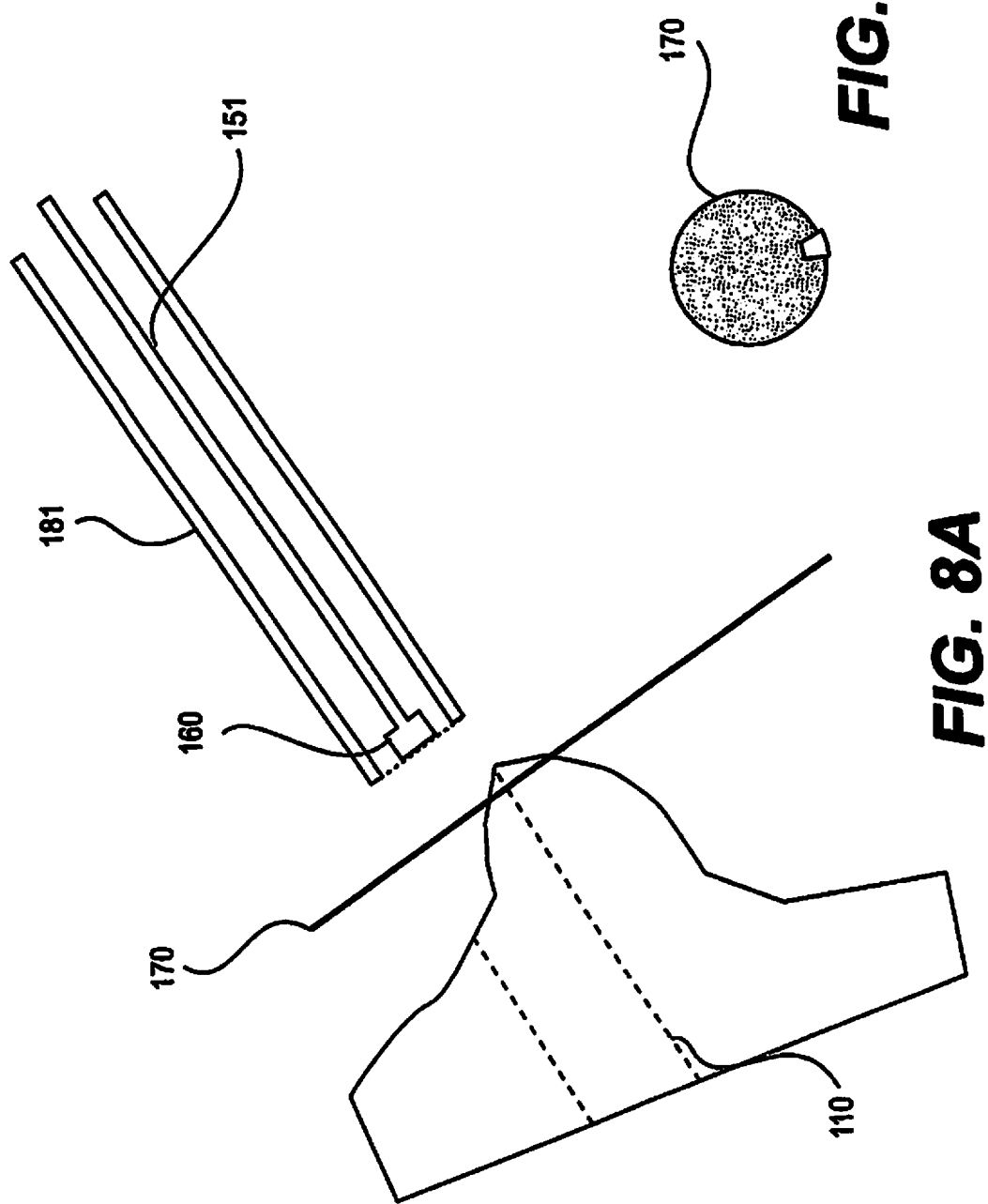

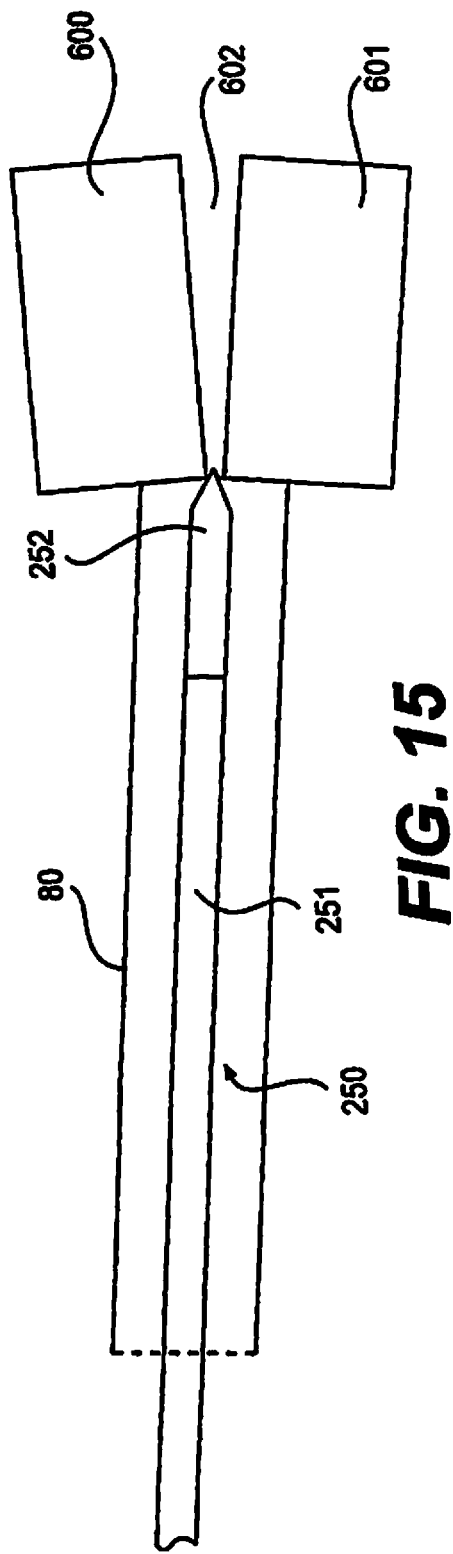
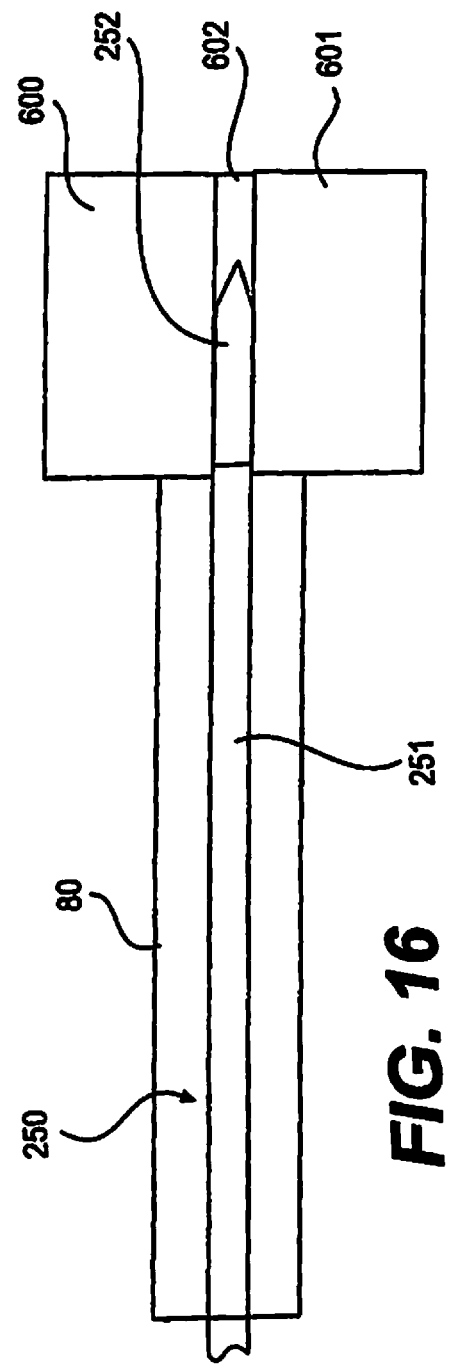

METHODS FOR PERFORMING MEDICAL PROCEDURES USING A SURGICAL ROBOT

CROSS-REFERENCE TO RELATED APPLICATIONS

This application is a continuation of U.S. application Ser. No. 16/708,545 filed on May 18, 2023, now U.S. Pat. No. 11,690,687, which is a continuation of U.S. application Ser. No. 14/476,101 filed on Sep. 3, 2014, now U.S. Pat. No. 10,531,927, which is a continuation of U.S. application Ser. No. 14/475,998 filed on Sep. 3, 2014, which is a continuation-in-part of U.S. application Ser. No. 13/924,505, entitled "Surgical Robot Platform," filed on Jun. 21, 2013, now U.S. Pat. No. 9,782,229, which claims priority to U.S. Application No. 61/800,527 filed on Mar. 15, 2013, and claims priority to U.S. Provisional Patent Application No. 61/662,702 filed on Jun. 21, 2012, all of which are incorporated herein by reference in their entireties for all purposes.

BACKGROUND

Embodiments are directed to a medical robot system. More particularly, embodiments are directed to a medical robot system including a robot coupled to an end-effectuator element with the robot configured to control movement and positioning of the end-effectuator in relation to the patient.

Various medical procedures require the precise localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes made up of non-planar curved surfaces making precise and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Robotic systems have been employed to help reduce tedious and time consuming processes. Many of the current robots used in surgical applications are specifically intended for magnifying/steadying surgical movements or providing a template for milling the bone surface. However, these robots are suboptimal for drilling holes and other related tasks.

Consequently, there is a need for a robot system that minimizes human and robotic error while allowing fast and efficient surgical access. The ability to perform operations on a patient with a robot system and computer software will greatly diminish the adverse effects upon the patient. The application of the robot system and the techniques used with the robot system may enhance the overall surgical operation and the results of the operation.

SUMMARY

Embodiments are directed to a method for removing bone with a robot system. The method may comprise extracting a two-dimensional slice from a three-dimensional computed tomography scan of a vertebra. The method may further comprise defining a perimeter on a pathway through the vertebra. The method may further comprise controlling a drill assembly with the robot system to remove bone from the pathway in the intersection of the perimeter and the two-dimensional slice.

Additional embodiments are directed to a method for inserting a tubular element into a patient with a robot system. The method may comprise loading computed tomography scans on to the robot system. The method may further comprise programming a route for the tubular element to travel through the patient to a section of the vertebra on a display, wherein the display may manipulate the robot system. The method may further comprise controlling the tubular element with the robot system to guide the tubular element along the programmed route through the patient.

Additional embodiments are directed to a method for aligning vertebrae for a surgical procedure using a robot system. The method may comprise inserting a tubular element into a patient and next to a disc space between adjacent vertebral bodies. The method may comprise attaching the tubular element to an end-effectuator of the robot system. The method may further comprise controlling a vertebral alignment tool with the robot system to insert the vertebral alignment tool through the tubular element such that vertebral alignment tool is inserted between the adjacent vertebral bodies to distract the adjacent vertebral bodies.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 8a illustrates a side cross-sectional view of a bony structure with a 2D slice through the bony structure indicated in accordance with one embodiment of the invention;

FIG. 8b illustrates a top end cross-sectional view of the 2D slice through the bony structure confined to the programmed perimeter in accordance with one embodiment of the invention;

FIG. 15 illustrate a vertebral alignment tool positioned outside two vertebral bodies in accordance with one embodiment of the invention;

FIG. 16 illustrates a vertebral alignment tool inserted into an intervertebral disc space, thereby aligning two vertebral bodies in accordance with one embodiment of the invention;

DETAILED DESCRIPTION

Figure 1:
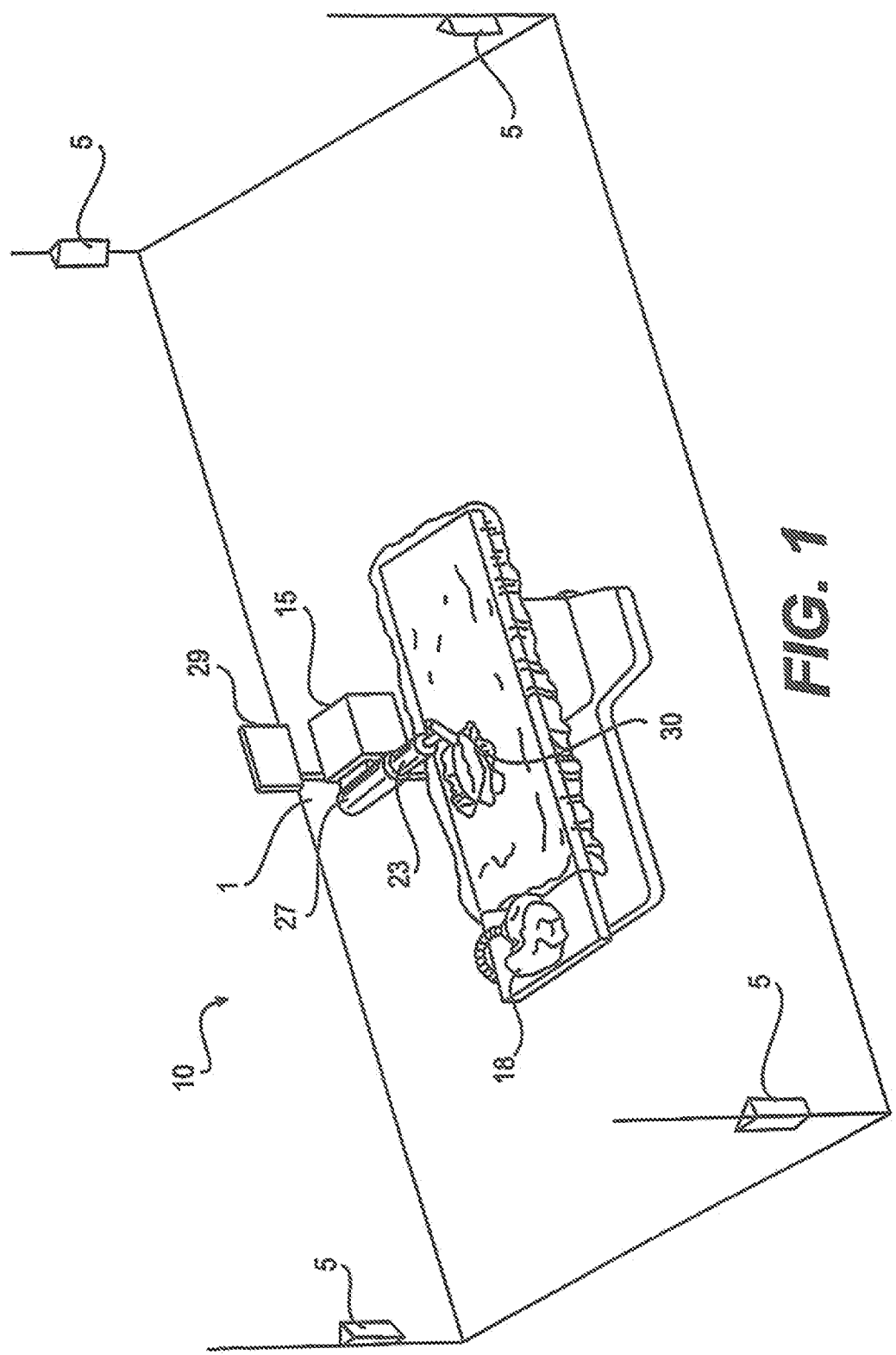
FIG. 1 illustrates a partial perspective view of a room in which a medical procedure is taking place by using a surgical robot.

In an embodiment, as illustrated in FIGS. 1-5, a surgical robot system 1 is disclosed in a room 10 where a medical procedure is occurring. In some embodiments, surgical robot system 1 may comprise a surgical robot 15, a display means 29, and a housing 27 to enclose a robot arm 23, and an end-effectuator 30 coupled to robot arm 23 controlled by at least one motor (not illustrated). In some embodiments a display means 29 may be attached to surgical robot 15, whereas in other embodiments, a display means 29 may be detached from surgical robot 15, either within surgical room 10 or in a remote location. In some embodiments, end-effectuator 30 may comprise a surgical instrument 35. In other embodiments, end-effectuator 30 may be coupled to surgical instrument 35. As used herein, the term "end-effectuator" is used interchangeably with the term "effectuator element." In some embodiments, end-effectuator 30 may comprise any known structure for effecting the movement of surgical instrument 35 in a desired manner.

In some embodiments, prior to performance of an invasive procedure, a three-dimensional ("3D") image scan may be taken of a desired surgical area of patient 18 and sent to a computer platform in communication with surgical robot 15. In some embodiments, a physician may then program a desired point of insertion and trajectory for surgical instrument 35 to reach a desired anatomical target within or upon the body of patient 18. In some embodiments, the desired point of insertion and trajectory may be planned on the 3D image scan, which in some embodiments, may be displayed on display means 29. In some embodiments, a physician may plan the trajectory and desired insertion point (if any) on a computed tomography scan (hereinafter referred to as "CT scan") of patient 18. In some embodiments, the CT scan may be an isocentric C-arm type scan, an O-arm type scan, or intraoperative CT scan as is known in the art. However, in some embodiments, any known 3D image scan may be used in accordance with the embodiments of robot system 1 described herein.

Figure 3:
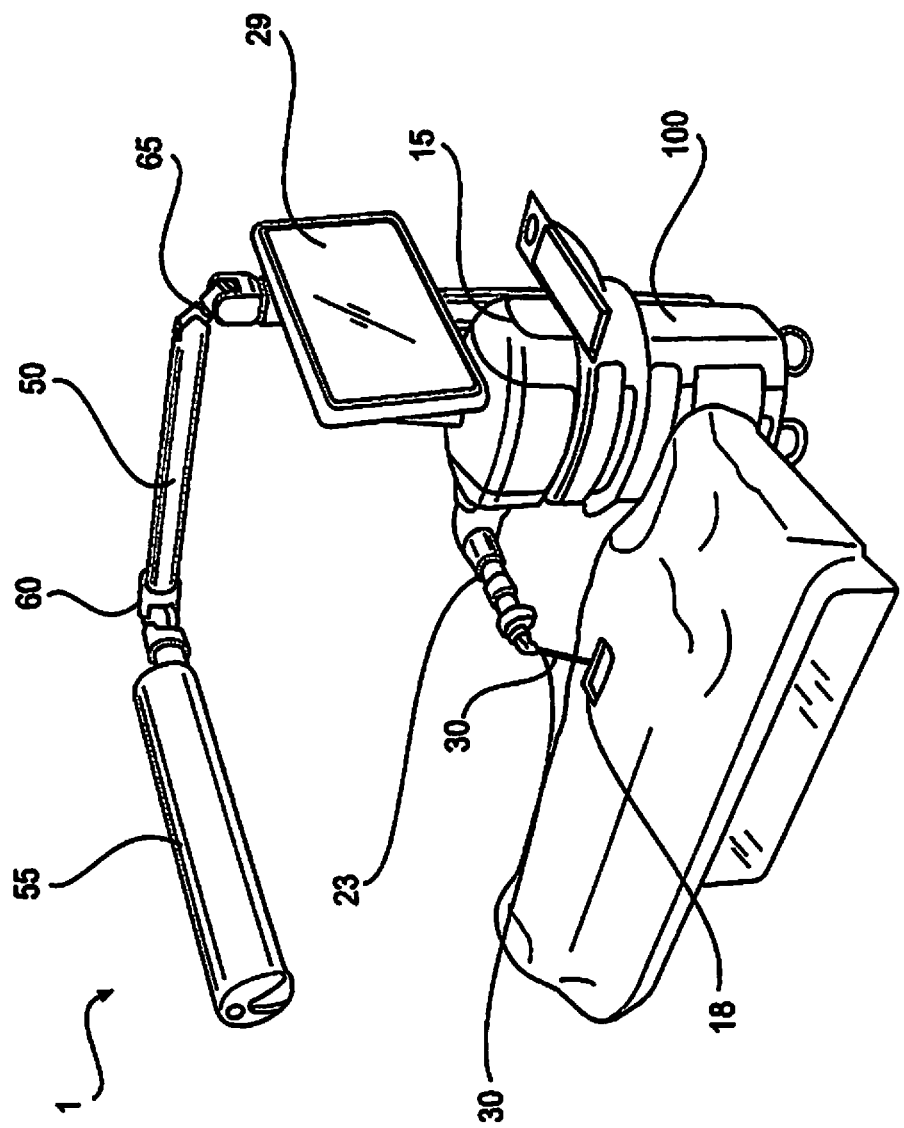
FIG. 3 illustrates a perspective view of a robot system including a camera arm in accordance with one embodiment of the invention.

In some embodiments, surgical robot system 1 may comprise a local positioning system ("LPS") subassembly to track the position of surgical instrument 35. In some embodiments, robot system 1 includes at least one mounted camera 56. For example, FIG. 3 illustrates a perspective view of a robot system 1 including a camera arm 55 in accordance with one embodiment of the invention. In some embodiments, to overcome issues with line of sight, it is possible to mount cameras 56 for tracking patient 18 and robot 15 on an arm 50 extending from the robot. As shown in FIG. 3, in some embodiments, arm 50 is coupled to a camera arm 55 via a joint 60, and arm 50 is coupled to robot system 1 via joint 65. In some embodiments, camera arm 55 may be positioned above a patient (for example, above patient 18 lying on a bed or stretcher as illustrated in FIG. 3). In this position, in some embodiments, it might be less likely for the surgeon to block the camera 56 when robot system 1 is in use (for example, during a surgery and/or patient examination). Further, in some embodiments, the joints 60, 65 may be used to sense the current position of the cameras 56 (i.e. the position of the camera arm 55). Moreover, in some embodiments, the exact position of end-effectuator 30 in the camera's 56 coordinate system may be calculated based on monitored counts on each robot axis, and in some embodiments, cameras 56 would therefore only have to collect data from tracked markers (not illustrated) on patient 18 to exactly calculate end-effectuator position relative to the anatomy.

Figure 4:
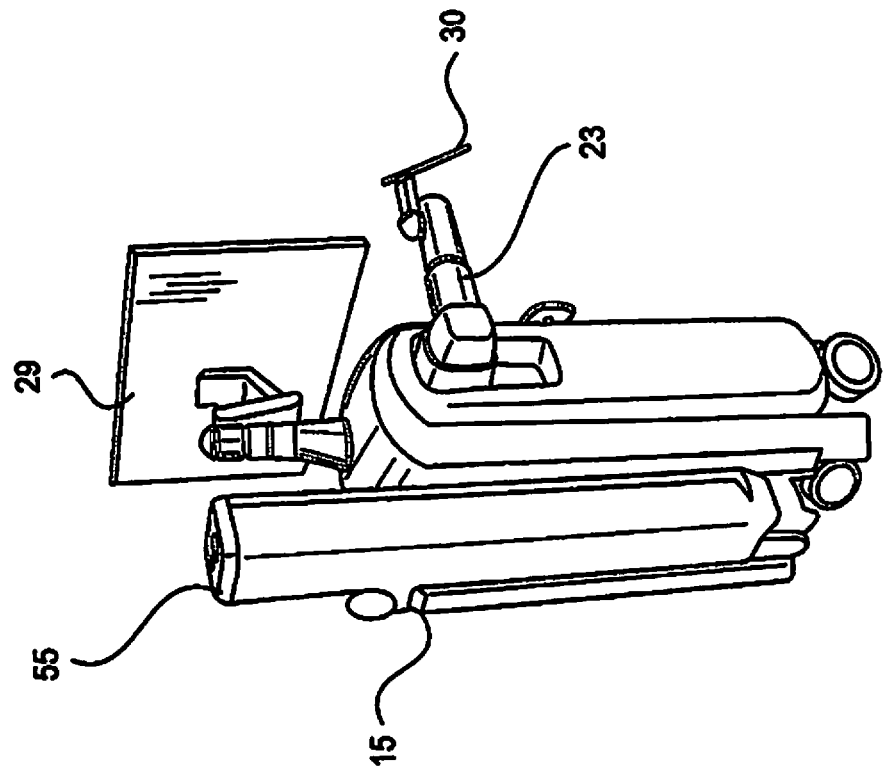
FIG. 4 illustrates a front-side perspective view of a robot system including a camera arm in a stored position in accordance with one embodiment of the invention.
Figure 5:
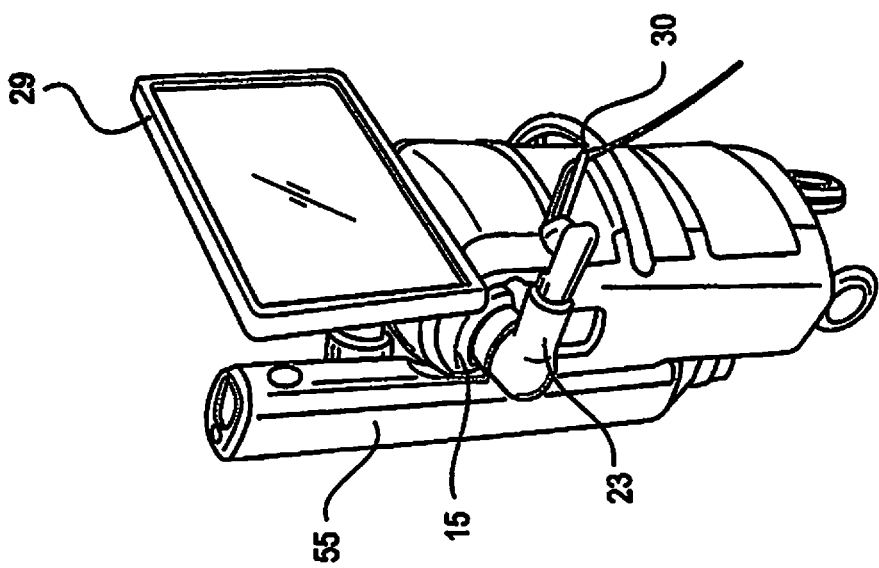
FIG. 5 illustrates a rear-side perspective view of a robot system including a camera arm in a stored position in accordance with one embodiment of the invention.

Some embodiments include an arm 50 and camera arm 55 that may fold into a compact configuration for transportation of robot system 1. For example, FIG. 4 illustrates a front-side perspective view of a robot system including a camera arm 55 in a stored position, and FIG. 5 illustrates a rear-side perspective view of a robot system including a camera arm 55 in a stored position in accordance with one embodiment of the invention.

In some embodiments, surgical robot system 1 may comprise a control device 100. In some embodiments, the processor of control device 100 may be configured to perform time of flight calculations of radiofrequency signals emitted at the surgical instrument 35 or end-effectuator 30 and received by wall-mounted receivers 5. Further, in some embodiments, robot system 1 may be configured to provide a geometrical description of the location of at least one bony structure such as a vertebra with respect to an operative end of surgical instrument 35 or end-effectuator 30 that is utilized to perform or assist in performing an invasive procedure. In some further embodiments, the position of vertebrae, as well as the dimensional profile of surgical instrument 35 or effectuator element 30 may be displayed on a monitor (for example on display means 29). In one embodiment, end-effectuator 30 may be a tubular element 80 (for example a cannula 121, dilator 200, probe 190, or guide tube) that is positioned at a desired location with respect to, for example, patient's 18 spine to facilitate the performance of a spinal surgery. In some embodiments, tubular element 80 may be aligned with a z axis defined by a corresponding robot motor (not illustrated) or, for example, may be disposed at a selected angle relative to the z-axis. In either case, the processor of control device 100 (i.e. a computer) may be configured to account for the orientation of tubular element 80 and the position of vertebrae. In some embodiments, the memory of control device 100 (i.e. a computer) may store software for performing the calculations and/or analyses required to perform many of the surgical method steps set forth herein. The software or a computer program may be provided on a tangible computer readable storage media, which is non-transitory in nature.

Another embodiment of the disclosed surgical robot system 1 involves the utilization of a robot 15 that is capable of moving end-effectuator 30 along x-, y-, and z-axes. In this embodiment, an x-axis may be orthogonal to a y-axis and the z-axis, the y-axis may be orthogonal to the x-axis and the z-axis, and the z-axis may be orthogonal to x-axis and y-axis. In some embodiments, robot 15 may be configured to effect movement of end-effectuator 30 along one axis independently of the other axes. For example, in some embodiments, robot 15 may cause end-effectuator 30 to move a given distance along the x-axis without causing any significant movement of end-effectuator 30 along the y-axis or the z-axis.

In some further embodiments, end-effectuator 30 may be configured for selective rotation about one or more of the x-axis, y-axis, and z-axis (such that one or more of the Cardanic Euler Angles (e.g., roll, pitch, and/or yaw) associated with end-effectuator 30 may be selectively controlled). In some embodiments, during operation, end-effectuator 30 and/or surgical instrument 35 may be aligned with a selected orientation axis that may be selectively varied and monitored by an agent (i.e. control device 100) that may operate surgical robot system 1. In some embodiments, selective control of the axial rotation and orientation of end-effectuator 30 may permit performance of medical procedures with significantly improved accuracy compared to conventional robots that utilize, for example, a six degree of freedom robot arm 23 comprising only rotational axes.

In some embodiments, as illustrated in FIG. 1, robot arm 23 may be positioned above the body of patient 18, with end-effectuator 30 selectively angled relative to the z-axis toward body of patient 18. In this aspect, in some embodiments, robotic surgical system 1 may comprise systems for stabilizing robotic arm 23, end-effectuator 30, and/or surgical instrument 35 at their respective positions in the event of power failure. In some embodiments, robotic arm 23, end-effectuator 30, and/or surgical instrument 35 may comprise a conventional worm-drive mechanism (not illustrated) coupled to robotic arm 23, configured to effect movement of robotic arm 23 along the z-axis. In some embodiments, the system for stabilizing robotic arm 23, end-effectuator 30, and/or surgical instrument 35 may comprise a counterbalance coupled to robotic arm 23. In another embodiment, the means for maintaining robotic arm 23, end-effectuator 30, and/or surgical instrument 35 may comprise a conventional brake mechanism (not illustrated) that is coupled to at least a portion of robotic arm 23, such as, for example, end-effectuator 30, and that is configured for activation in response to a loss of power or "power off" condition of surgical robot 15.

In some embodiments, control device 100 is also in communication with surgical robot 15. In some embodiments, a conventional processor (not illustrated) of control device 100 may be configured to effect movement of surgical robot 15 according to a preplanned trajectory selected prior to the procedure. For example, in some embodiments, controlling device 100 may use robotic guidance software (not illustrated) and robotic guidance data storage (not illustrated) to effect movement of surgical robot 15.

In some embodiments, the position of surgical instrument 35 may be dynamically updated so that surgical robot 15 is aware of the location of surgical instrument 35 at all times during the procedure. Consequently, in some embodiments, surgical robot 15 may move surgical instrument 35 to the desired position quickly, with minimal damage to patient 18, and without any further assistance from a surgeon (unless the surgeon so desires). In some further embodiments, surgical robot 15 may be configured to correct the path of surgical instrument 35 if surgical instrument 35 strays from the selected, preplanned trajectory.

In some embodiments, surgical robot 15 may be configured to permit stoppage, modification, and/or manual control of the movement of end-effectuator 30 and/or surgical instrument 35. Thus, in use, in some embodiments, an agent (e.g., surgeon, a physician or other user) that may operate robot system 1 has the option to stop, modify, or manually control the autonomous movement of end-effectuator 30 and/or surgical instrument 35. Further, in some embodiments, tolerance controls may be preprogrammed into surgical robot 15 and/or control device 100 (such that the movement of the end-effectuator 30 and/or surgical instrument 35 is adjusted in response to specified conditions being met). For example, in some embodiments, if surgical robot 15 cannot detect the position of surgical instrument 35 because of a malfunction in the LPS system, then surgical robot 15 may be configured to stop movement of end-effectuator 30 and/or surgical instrument 35. In some embodiments, if surgical robot 15 detects a resistance, such as a force resistance or a torque resistance above a tolerance level, then surgical robot 15 may be configured to stop movement of end-effectuator 30 and/or surgical instrument 35.

In some embodiments, control device 100, as further described herein, may be located within surgical robot 15, or, alternatively, in another location within surgical room 10 or in a remote location. In some embodiments, control device 100 may be positioned in operative communication with cameras 56, for tracking, and surgical robot 15.

In some further embodiments, surgical robot 15 may also be used with existing conventional guidance systems. Thus, alternative conventional guidance systems beyond those specifically disclosed herein are within the scope and spirit of the invention. For instance, a conventional optical tracking system (not illustrated) for tracking the location of the surgical device, or a commercially available infrared optical tracking system (not illustrated), such as Optotrak® (Optotrak® is a registered trademark of Northern Digital Inc. Northern Digital, Waterloo, Ontario, Mayada), may be used to track patient's 18 movement and robot's base 25 location and/or intermediate axis location, and used with surgical robot system 1. In some embodiments in which surgical robot system 1 comprises a conventional infrared or visible light optical tracking system (not illustrated), surgical robot system 1 may comprise conventional optical markers attached to selected locations on end-effectuator 30 and/or surgical instrument 35 that are configured to emit or reflect light. In some embodiments, the light emitted from and/or reflected by the markers may be read by cameras 56 and/or optical sensors and the location of the object may be calculated through triangulation methods (such as stereophotogrammetry).

Figure 2:
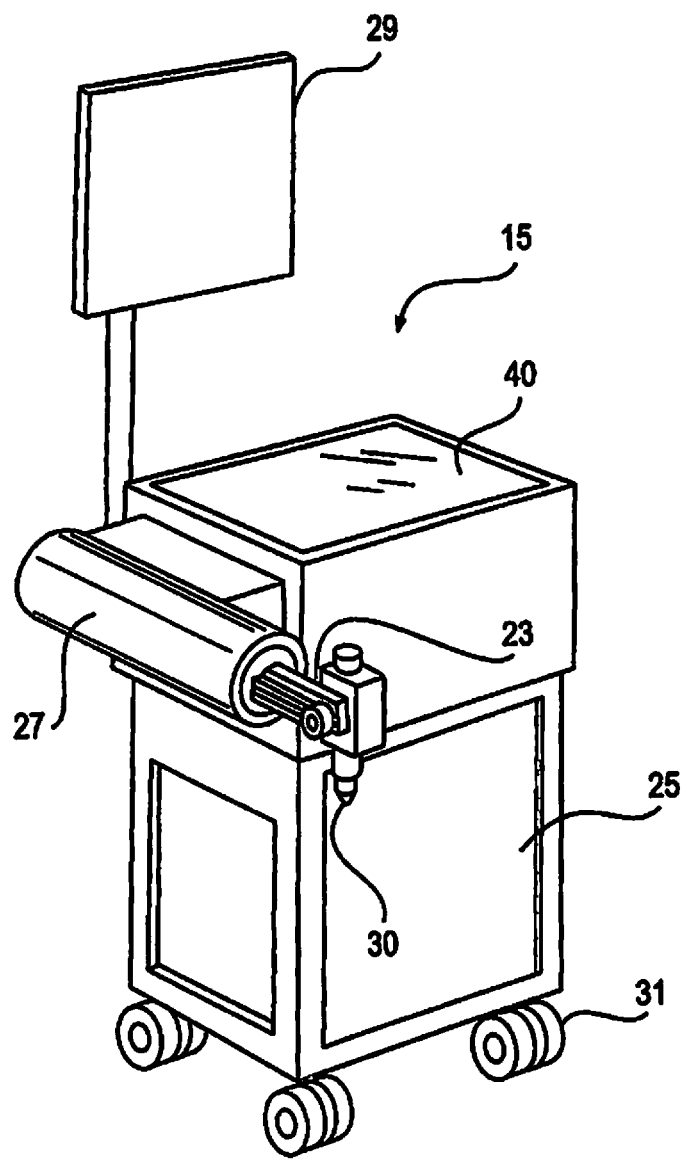
FIG. 2 illustrates a perspective view of a surgical robot according to an embodiment of the invention.

Illustrated in FIG. 2, it is seen that, in some embodiments, surgical robot 15 may comprise a base 25 connected to wheels 31. The size and mobility of these embodiments may enable the surgical robot to be readily moved from patient to patient and room to room as desired. As shown, in some embodiments, surgical robot 15 may further comprise a case 40 that is slidably attached to base 25 such that case 40 may slide up and down along the z-axis substantially perpendicular to the surface on which base 25 sits. In some embodiments, surgical robot 15 may include a display means 29, and a housing 27 which contains robot arm 23.

As described earlier, end-effectuator 30 may comprise a surgical instrument 35, whereas in other embodiments, end-effectuator 30 may be coupled to surgical instrument 35. In some embodiments, arm 23 may be connected to end-effectuator 30, with surgical instrument 35 being removably attached to end-effectuator 30.

In some embodiments, robot system 1 may be used in common spinal surgery procedures such as Transforaminal Lumbar Interbody Fixation ("TLIF"), Posterior Lumbar Interbody Fixation ("PLIF"), Lateral Lumbar Interbody Fixation ("LLIF"), laminectomy or foraminotomy procedures. Robot system 1 may be used in any of the above mentioned approaches where bone removal may be needed. Specifically, robot system 1 may be able to target selected areas of bone for milling. Robot system 1 may further be registered to patient 18. In some embodiments, the means for registering may comprise radio-opaque fiducial markers and optical tracking markers rigidly attached to a patient-mounted fixture. Locations of fixture's fiducial markers on the 3D image may be related to tracked locations of the fixture's optical tracking markers to co-register camera 56 and medical image coordinate systems. In still further embodiments, cameras 56 may be used for tracking the location of the end-effectuator 30 or surgical instrument 35 in relation to the patient. Cameras 56 that may be used are to be similar to those used by the StealthStation® S7®, StealthStation i7™, or StealthStation iNav®, which track light-emitting or reflective markers using stereophotogrammetry. (StealthStation® S7®, StealthStation i7™, or StealthStation iNav® are registered trademarks of Medtronic, Inc.) Cameras 56 may be located on camera arm 55, see FIG. 2, or stationed around patient 18. Once registered to patient 18, robot system 1 may very accurately gauge its end-effectuator's 30 location relative to any layer of bone viewable on a CT.

Figure 6:
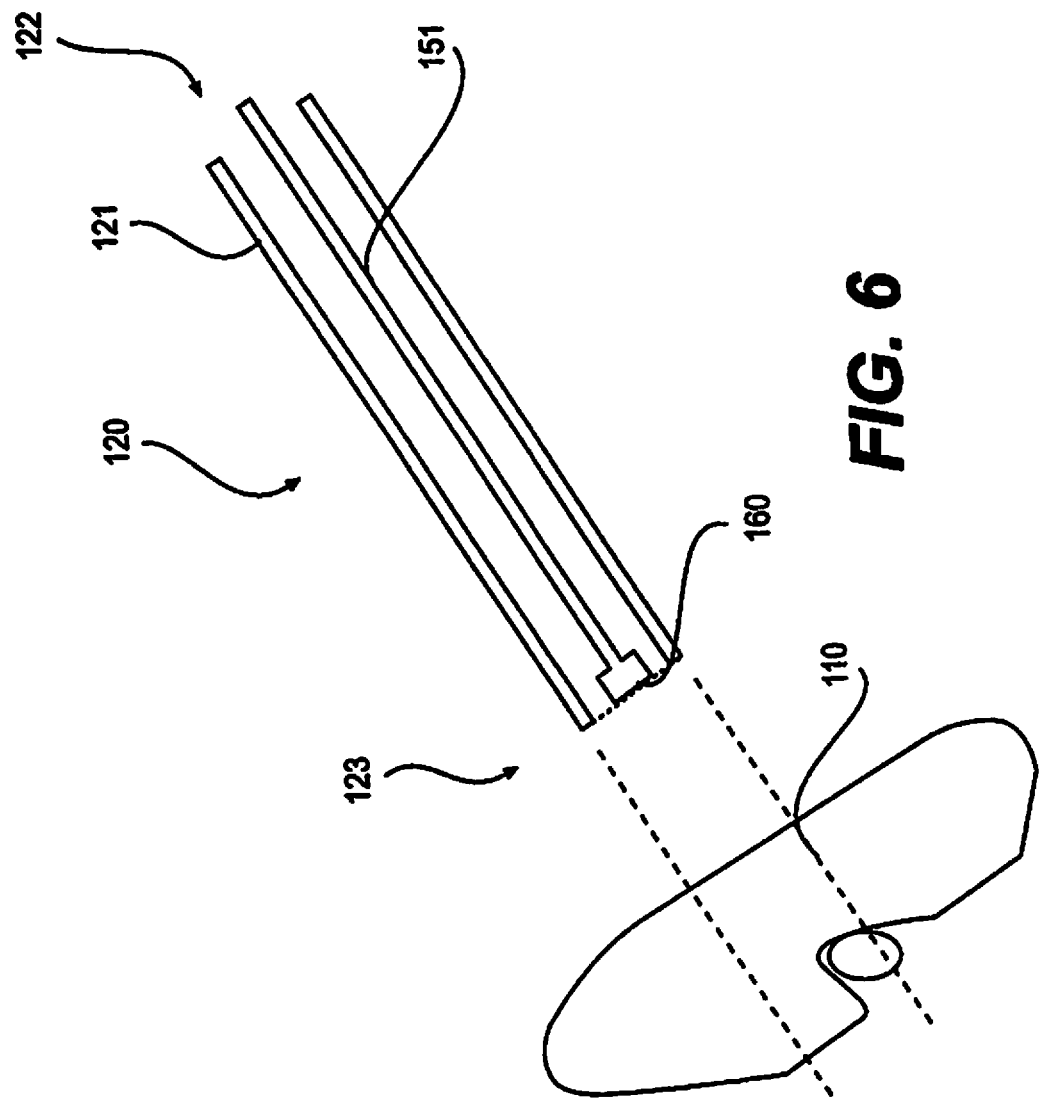
FIG. 6 illustrates a side cross-sectional view of a bony structure and critical structure with a milling bit inside a cannula positioned adjacent to the bony structure in accordance with one embodiment of the invention.

Embodiments of spine surgery techniques may include creating an access channel between two vertebral bodies or through bone. FIG. 6 illustrates a cannula assembly 120 that may be used to create an access channel through the tissue of patient 18 to target anatomy in accordance with one embodiment of robot system 1. In the illustrated embodiment, the cannula assembly 120 comprises a cannula 121 configured to allow passage of various instruments and materials through the pathway to target anatomy. The cannula may have an inside diameter just large enough to pass a drill bit or needle, or an inside diameter large enough to pass implants such as interbody grafts used in TLIF, PLIF, or LLIF. Cannula 121 may have a proximal end 122 and a distal end 123. Cannula assembly 120 further may include a drill assembly which may be removed from cannula 121. As illustrated in FIG. 6, drill shaft 151 may be positioned in cannula 121 with milling bit 160 positioned at distal end 123. Drill assembly (not pictured) may further comprise a motor, a body, and parts known to one of ordinary skill in the art. In an embodiment, cannula assembly 120 may further comprise a handle (not illustrated) disposed on the proximal end 122 of cannula 121. In an embodiment, cannula assembly 120 may be a trocar-tipped cannula. By way of example, cannula assembly 120 may be a diamond, scoop, bevel, or trocar tipped cannula.

To create an access channel, the surgeon, for example, may make an incision in the back of patient 18. Distal end 123 of cannula 121 may be inserted into the incision. The surgeon may then apply longitudinal force to cannula assembly 120 while rotating the handle to advance cannula 121 through the soft tissue of patient 18 and cause distal end 123 to abut or penetrate into a bony structure. In an embodiment, cannula 121 may be inserted into the vertebral body through a pedicle (not illustrated). Once cannula 121 has been inserted to the necessary depth, the handle may be removed, leaving cannula 121. In this manner, cannula 121 may provide an access channel into the target site.

Figure 11:
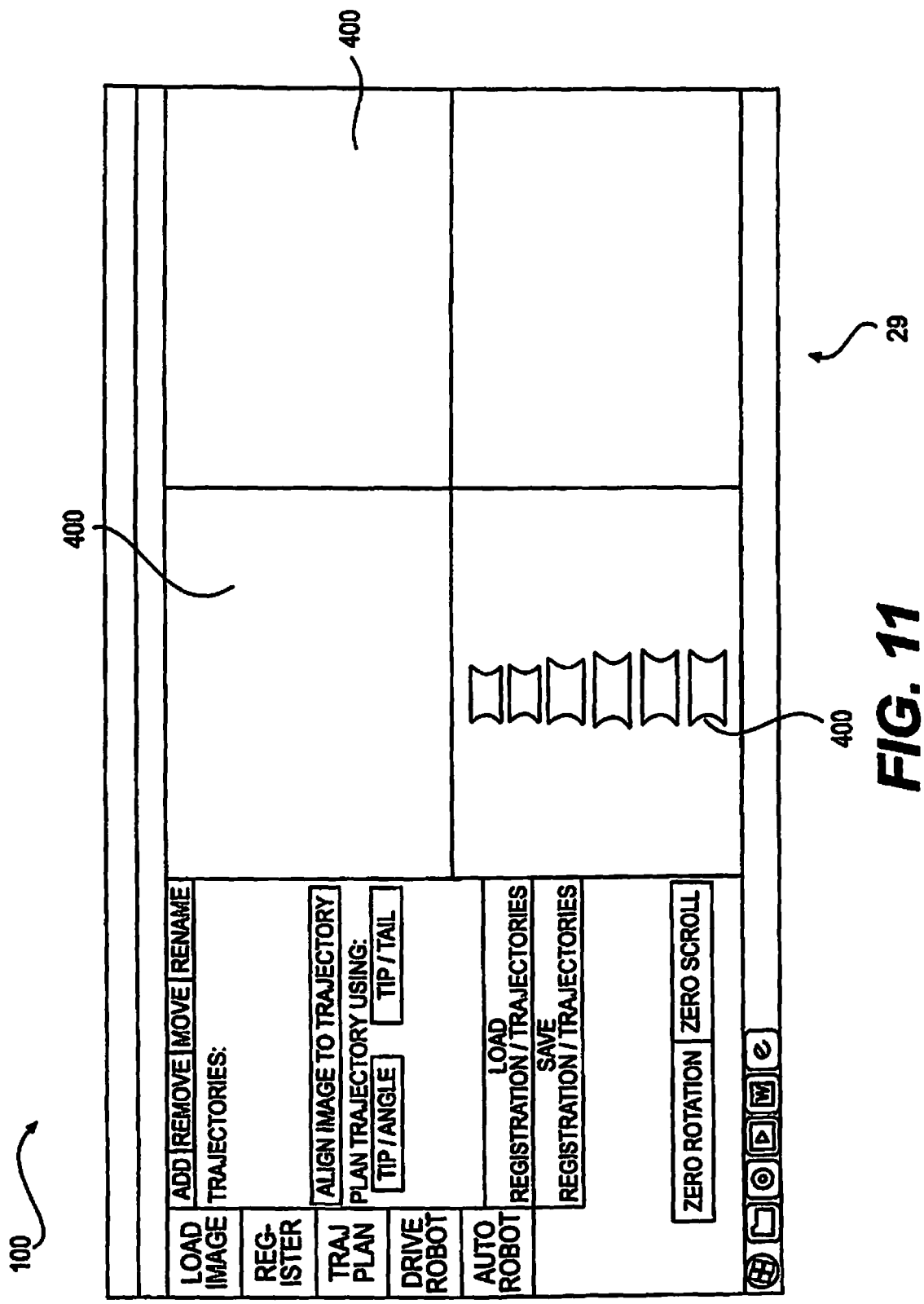
FIG. 11 illustrates a computerized display used to program the route of tubular element by a robot system in accordance with one embodiment of the invention.

In a similar method, to form an access channel, the surgeon may make an incision in the back of patient 18. Proximal end 122 of cannula 121 may be attached to robot system 1 by way of end-effectuator 30. As described above, CT scans of patient 18 may be loaded to control device 100. Once loaded, control device 100 may register robot system 1, end-effectuator 30, CT scans of patient 18, and the current position of patient 18 on control device 100. Once registration on control device 100 is complete, the surgeon may program robot system 1 to align cannula 121 to a desired trajectory line 400 through patient 18 to a target site. As illustrated in FIG. 11, the surgeon may designate a trajectory line 400 on control device 100, using display means 29, to reach the interbody space between two vertebral bodies. The robot system 1 may then control the cannula 121 to place the cannula 121 into patient 18 along the programmed trajectory. The surgeon may then insert a probe (not illustrated) through cannula 121 to monitor nerve activity. If adjustments to the trajectory are needed the surgeon may alter trajectory line 400 on control device 100 to an alternate position by means of control device 100, through an interface on display means 29. Robot system 1 may then immediately shift trajectory line 400 along new trajectory line 400. Control device 100 may be enabled to automatically shift trajectory line 400 away from neural activity, as provided by the probe, which may have reached a critical threshold. This automatic shift may allow tubular element 80 to reach the intervertebral disc space with a greater ability of avoiding nerves and causing nerve damage.

While cannula assembly 120 may be suited for creating an access channel to vertebral bodies or intervertebral disc spaces in all regions of the vertebral column, cannula assembly 120 may be particularly suited for access in the middle and lower areas of the thoracic region. If access is desired from the middle of the thoracic region and above, a device having a tapered cannula (not illustrated) may be used. While the tapered cannula may be particularly suited for accessing the middle of the thoracic region and above, it should be understood that the tapered cannula may also be used to create an access channel to vertebral bodies in all regions of the vertebral column.

Figure 7B:
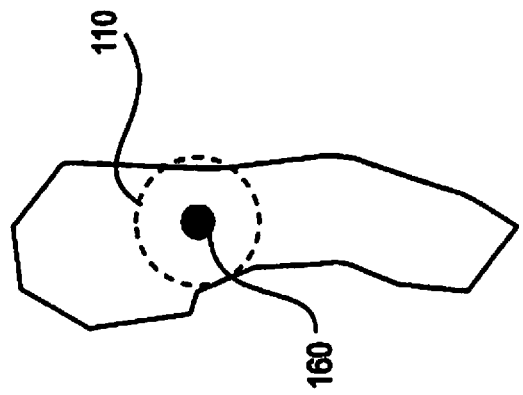
FIG. 7b illustrates a top end cross-sectional view of the same bony structure as FIG. 7a with a programmed perimeter in accordance with one embodiment of the invention.
Figure 7A:
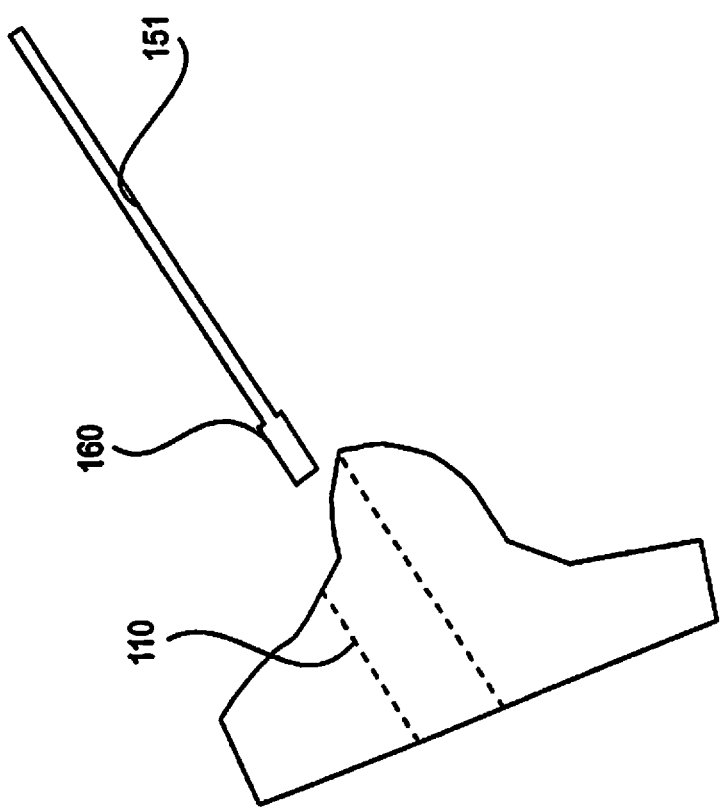
FIG. 7a illustrates a side cross-sectional view of a bony structure and a milling bit with a programmed perimeter in accordance with one embodiment of the invention.

After cannula 121 has been inserted and correctly positioned inside the body of patient 18, a drill assembly 500 may be inserted into cannula 121. The drill assembly 500 may comprise drill shaft 151, milling bit 160, and may further comprise a motor, a body, and parts known to one of ordinary skill in the art. Drill assembly 500 may attach to end-effectuator 30 by any suitable means. Furthermore, drill assembly 500 may be attached to end-effectuator 30 before insertion of cannula 121 or after insertion of cannula 121 into patient 18. As illustrated in FIGS. 7a and 7b, a surgeon may use control device 100 to define a perimeter 110 around an area within which the surgeon may desire to remove some bone with drill assembly 500. Perimeter 110 may be of any suitable shape or design the surgeon chooses. Without limitation, a suitable perimeter shape may be round, square, rectangular, any surgeon hand drawn enclosure, or any combination thereof. In one embodiment, perimeter may match the circular shape of the outer diameter of the cannula. As illustrated in FIG. 7a, a side view of the bony structure illustrates the outer edges of perimeter 110. An end-on view, as illustrated in FIG. 7b, illustrates the area of perimeter 110 in which milling bit 160 may operate. Uploading perimeter 110 into control device 100 may instruct end-effectuator 30 to prevent milling bit 160 from moving outside perimeter 110.

Figure 9:
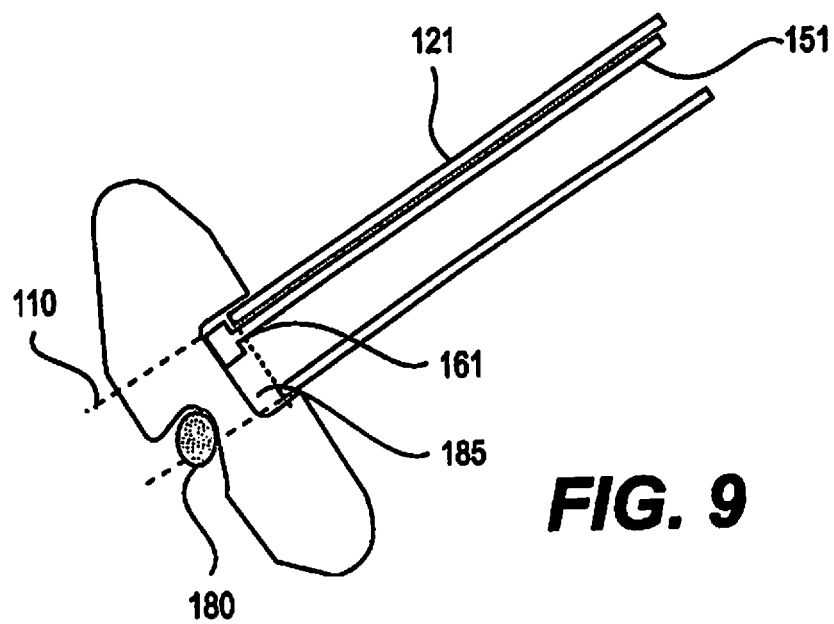
FIG. 9 illustrates a side cross-sectional view of a bony structure with the milling bit extending out of a cannula removing bone in accordance with one embodiment of the invention.

After perimeter 110 is loaded, control device 100 may then proceed to remove bone. By way of example, the control device 100 of the robot system 1 may control the drill assembly 500 for bone removal. In some embodiments, the control device 100 may turn on the drill assembly 500. Turning "on" the drill assembly may rotate milling bit 160 at about 500 to about 30,000 RPM, for example. Before removing bone, control device 100 may assess the demarcation between bone and soft tissue on a 2D reformatted slice (reslice) of uploaded CT volume of the anatomy inside patient 18. As illustrated in FIGS. 8a and 8b, reslice plane 170 may be perpendicular to the approach pathway but could alternately be perpendicular to the axis of the drill shaft 151, the axis of the cannula 121, or any suitable axis. Surgeon may instruct control device 100 to iteratively move reslice plane 170 distally down the axis of approach and distal to milling bit 160 before milling bit 160 advances. Control device 100 may display an image of reslice plane 170 as it advances. As illustrated in FIG. 8, the surgeon may halt advancement and display of the reslice plane 170 at a position where the first bone is to be encountered. Control device 100 may be used to monitor exact location of drill bit 160 relative to the anatomy while surgeon advances cannula 121 to a known position relative to reslice plane 170 and drill bit 160. In one embodiment, this known position may be proximal to the reslice plane by the head depth of the drill bit 160. As illustrated in FIG. 8b, an end-on view illustrates the cross section of reslice plane 170 and perimeter 110. The area in white is bone that may be removed by milling bit 160 and the area in black is soft tissue. In one embodiment, grayscale thresholding may be used to automatically assess and delineate white from black regions, providing data to control device 100 to automatically set boundaries for allowing or preventing drilling in different regions in this plane and bounded by perimeter 110. In another embodiment, the surgeon uses a software interface to manually mark bone and soft tissue areas on reslice plane 170. In one embodiment, control device 100 may enable drill shaft's 151 position to be moved laterally while maintaining angular orientation. Control device 100 may also only allow the drill bit to advance distally past the cannula tip if it is in the region in white but not in the region in black. In another embodiment, control device 100 may enable rotation of drill shaft 151 and may have it coupled with translation so that milling bit 160 position stays in reslice plane 170. Control device 100, with perimeter 110, may prevent drilling in any region that is not bone and allow removal of bone that is present within the cross section of perimeter 110 and reslice plane 170. The milling bit 160 may be advanced to remove bone distal to the cannula 121. In one embodiment, to limit bone removal to a region that has been viewed on resliced CT, the milling bit 160 is advanced only until it reaches the reslice plane 170. As illustrated in FIG. 9, because the milling bit diameter is larger than the drill shaft diameter, milling bit 160 may be advanced to remove bone lateral to cannula 121 by the distance from the outer edge of the drill shaft 151 to the outer edge of the milling bit 160. This feature may allow for milling bit 160 to remove enough bone for cannula 121 to advance through or past the bony structure after bone is removed from in front of the cannula's leading edge. After removal of bone between cannula tip and reslice plane 170, which may be assessed by recording the area removed manually or on control device 100 by monitoring the registered position of end-effectuator and path of the bit, the surgeon may manually advance the cannula 121 into vacated space 185. A new reslice plane 170 on the CT scan of patient 18 may then be assessed from the existing CT scan volume by control device 100. In other embodiments, robot system 1 may assess multiple reslice planes 170 of the CT scan of patient 18 at the same time. The use of multiple reslice planes 170 may "look ahead" of milling bit 160. Viewing sequential slices in the path ahead of the current cannula location may alert the surgeon to a critical structure 180 that would harm patient 18 if removed by milling bit 160. As illustrated on FIG. 9, the milling bit 160, which is connected to end-effectuator 30, may be advanced into or past bony structures in advance of the cannula 121. The milling bit 160 may remove bone allowing the cannula 121 to be advanced into or past the bony structure. Without the bone structures to block it, the cannula 121 would be pushed past soft tissues, which were not drilled, pushing these tissues aside as commonly occurs with cannula insertion.

Figure 10:
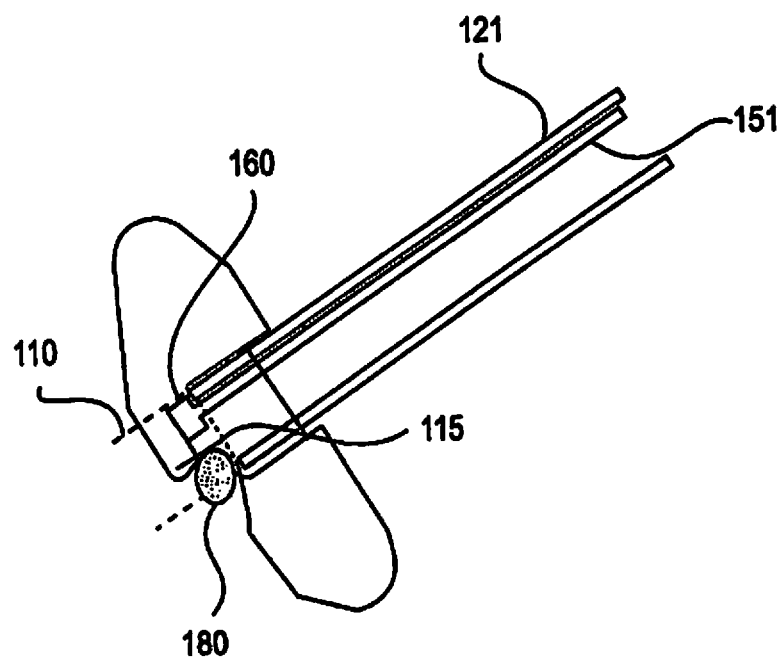
FIG. 10 illustrates a side cross-sectional view of a bony structure with the milling bit extending out of a cannula and removing bone from around a critical structure in accordance with one embodiment of the invention.

As illustrated in FIG. 10, a reslice plane 170 may eventually reveal critical structure 180. Control device 100 may alert the surgeon to critical structure 180. A critical structure 180 may be, but is not limited to, a nerve, blood vessel, tumor, fracture, muscle, tendon, or any combination thereof into which one of ordinary skill in the art would not want to drill. The surgeon may then create a second perimeter 115. Second perimeter 115 may be plotted around critical structure 180. Second perimeter 115 may be of any suitable shape or design the surgeon chooses. Without limitation, a suitable shape may be round, square, rectangular, any surgeon hand drawn enclosure, or any combination thereof. Second perimeter 115 may be loaded into control device 100. Control device 100 may then prevent milling bit 160 or cannula 121 from entering the area defined by second perimeter 115. This second perimeter may allow for milling bit 160 to continue removing bone from around critical structure 180 without harming critical structure 180. As illustrated in FIG. 10, critical structure 180 may prevent cannula 121 from advancing farther into the patient. In this respect, the critical structure is treated differently than soft tissues appearing as black on the reslice plane—with the soft tissues, the surgeon continues to advance the cannula forward and pushes them aside whereas with a critical structure, cannula advancement must stop. Milling bit 160 may continue to remove bone farther into the bony structure by staying within the bounds of perimeter 110, outside of second perimeter 115.

Figure 12:
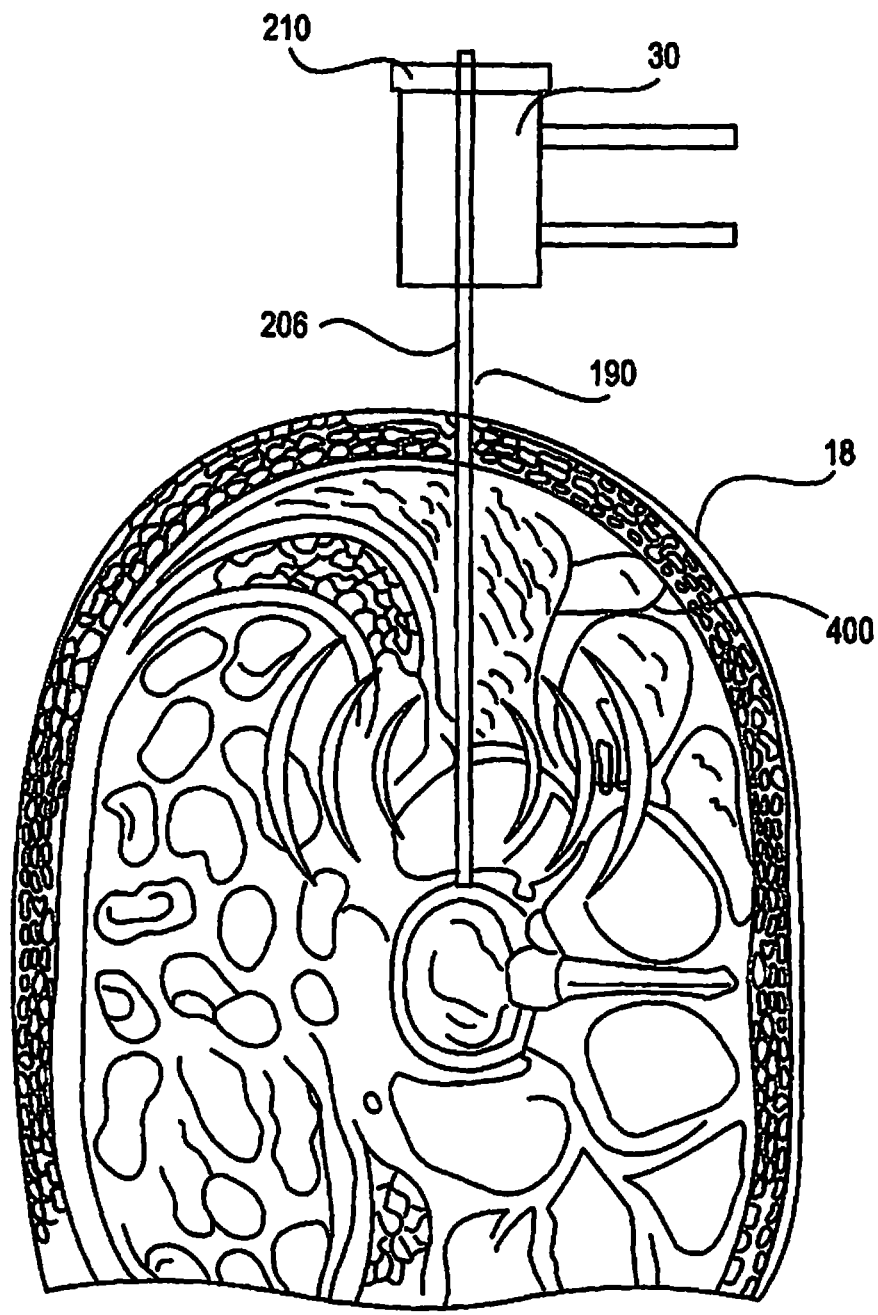
FIG. 12 illustrates a center tool held by an end-effectuator and positioned next to an intervertebral disc space in accordance with one embodiment of the invention.

In some embodiments, robot system 1 may be used during LLIF operations. Current technology requires an LLIF access portal to be established. Portal placement is normally accomplished by a surgeon who inserts a probe from a lateral approach and guides the probe toward the disc space, adjusting the path as needed to steer the probe away from nerves in the psoas muscle and exiting the spine. As illustrated in FIG. 12, robot system 1 may be used to move or guide manual movement of a center tool 190 through patient 18 during a LLIF procedure. Further illustrated in FIG. 12 are end-effectuator 30, spacer 210, dilator 200, and trajectory line 400. End-effectuator 30 is attached to robot system 1 and may be used to guide center tool 190 or hold center tool 190 and dilators 200 in place. End-effectuator 30 may grasp center tool 190 or dilators 200 by way of spacer 210 or any other means known to one skilled in the art. Spacer 210 may be removed and replaced as necessary to properly attach center tool 190 or dilators 200 to end-effectuator 30. As described above, patient 18 and CT scan volume of patient 18 may be registered together through control device 100. The surgeon may then plot trajectory line 400 on control device 100 through display means 29, which may display key anatomical views generated from the CT scans. Robot system 1 may align trajectory line 400 based upon the surgeon's inputs. The surgeon may insert a probe (not illustrated) through center tool 190 to monitor nerve activity as center tool 190 is maneuvered through patient 18 by robot system 1. If an adjustment to trajectory line 400 of center tool 190 is required, the surgeon may re-plot trajectory line 400 to an alternate position on control device 100, through display means 29. Robot system 1 may immediately correct trajectory line 400 of center tool 190, based upon re-plotting of trajectory line 400. Furthermore, control device 100 may be programmed to automatically shift trajectory line 400 of center tool 190 away from areas where neural activity has reached a critical threshold as measured by the probe inserted in center tool 190. After placement of center tool 190 against an intervertebral disc space, dilators 200 may be used to expand the working space available to a surgeon.

Figure 13A:
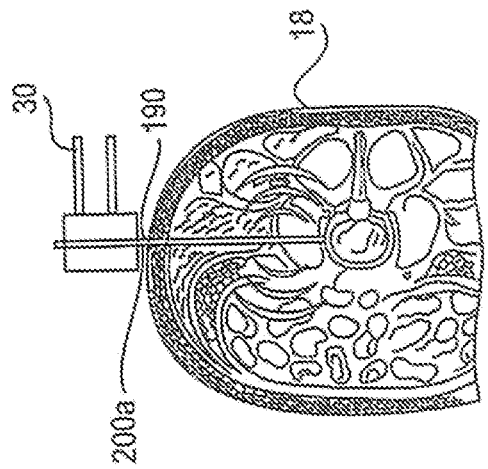
FIG. 13a illustrates the spacer being removed from the end-effectuator in accordance with one embodiment of the invention.
Figure 13B:
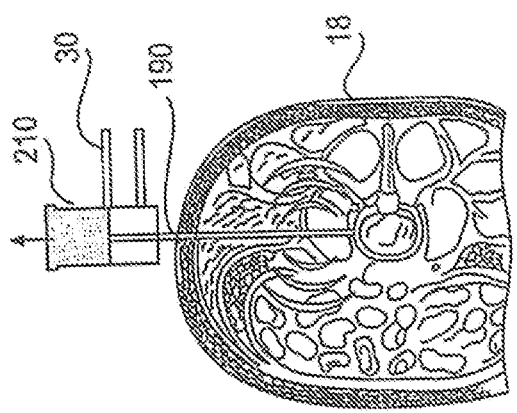
FIG. 13b illustrates a first dilator being positioned over a center tool in accordance with one embodiment of the invention.
Figure 13C:
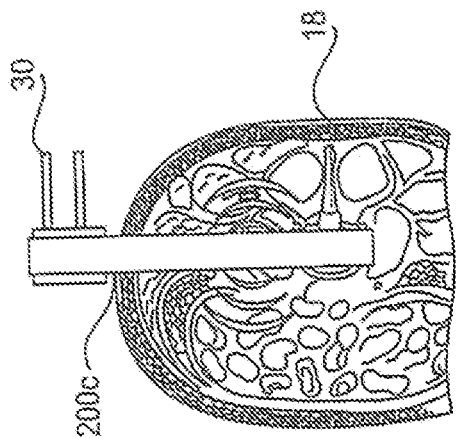
FIG. 13c illustrates a second dilator being positioned over a previously positioned dilator in accordance with one embodiment of the invention.
Figure 13D:
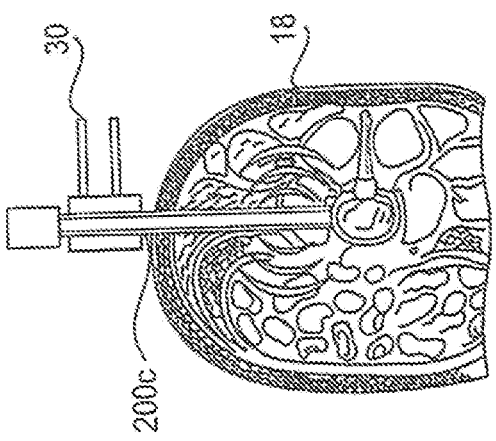
FIG. 13d illustrates a third dilator being positioned over a previously positioned dilator in accordance with one embodiment of the invention.
Figure 13E:
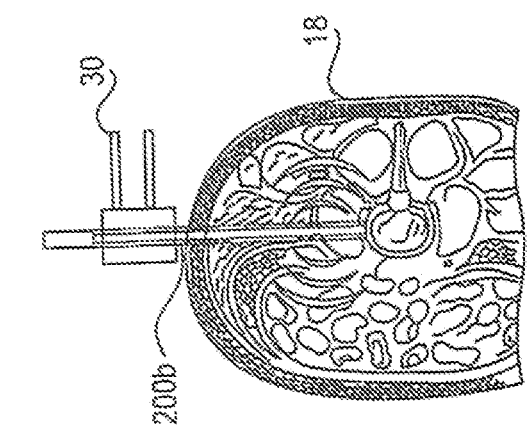
FIG. 13e illustrates the removal of a center tool and other dilators, with the largest dilator remaining in the patient in accordance with one embodiment of the invention.

As illustrated in FIGS. 13*a*, 13*b*, 13*c*, 13*d*, and 13*e*, after center tool 190 has reached the intended intervertebral disc space, one or more dilators 200*a*, 200*b*, or 200*c* may be maneuvered down the length of center tool 190 to the intervertebral disc space. Center tool 190 and dilators 200 may be held in position by spacer 210. Spacer 210 may align center tool 190 and dilators 200 to end-effectuator 30. As illustrated in FIG. 13*a*, spacer 210 may be removed to allow for the insertion of dilators 200*a*, 200*b*, and 200*c*. As illustrated in FIG. 13*a*, center tool 190 may be positioned against the intervertebral disc space in patient 18 by end-effectuator 30. After center tool 190 has been positioned, spacer 210 may be removed for the insertion of dilators to increase the work space available to a surgeon. Illustrated in FIG. 13*b*, dilator 200*a*, which may have inside diameter slightly larger than outside diameter of center tool 190, may be placed around center tool 190 and moved down center tool 190 until adjacent to the intervertebral disc space in patient 18. FIG. 13*c* illustrates the same process in FIG. 13*b* with dilator 200*b* being slightly larger and moved along dilator 200*a*. FIG. 13*d* illustrates the same process in FIG. 13*c* with dilator 200*c* being slightly larger and moved along dilator 200*b*. These steps may be repeated multiple times as desired by the surgeon (additional steps may not be pictured). As illustrated in FIG. 13*e*, after dilators 200*a*, 200*b*, and 200*c* have been placed, center tool 190 and dilators 200*a* and 200*b* may be removed. This removal may leave dilator 200*c* attached to end-effectuator 30, creating a working space for a surgeon to operate in.

Figure 14:
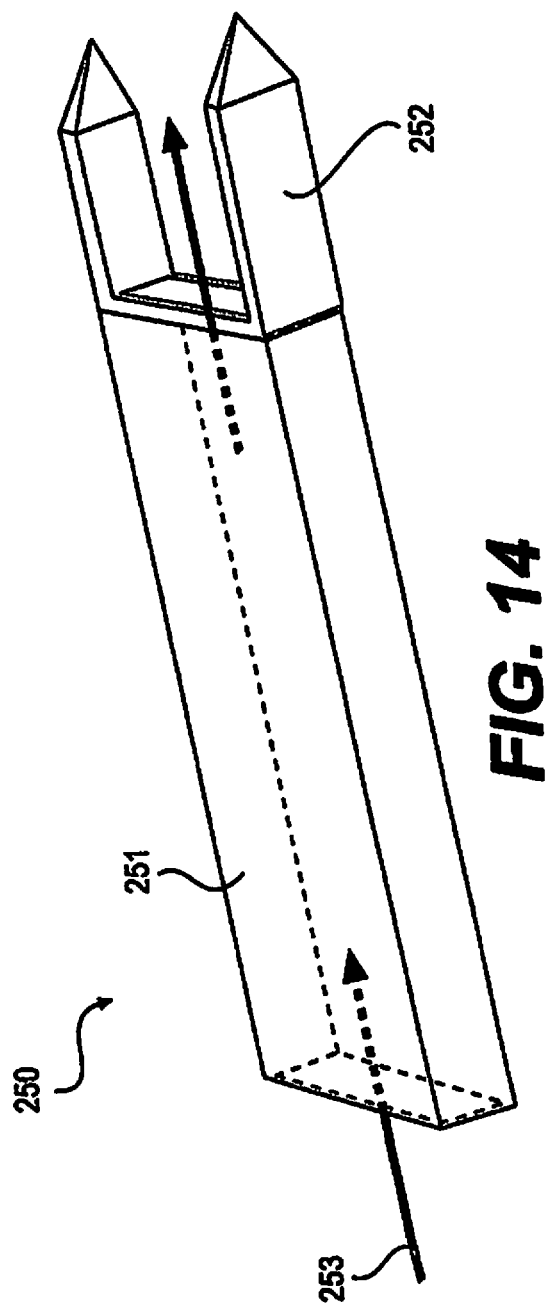
FIG. 14 illustrates a vertebral alignment tool with a working channel in accordance with one embodiment of the invention.

FIG. 14 illustrates a vertebral alignment tool 250, which may be used after insertion of tubular element 80, in certain embodiments. Vertebral alignment tool 250 may be used to prepare the intervertebral disc space of patient 18 for further surgical operations. As illustrated in FIG. 14, vertebral alignment tool 250 may comprise a body 251, a penetrating end 252, and a working channel 253. Body 251 may be of any suitable width to fit within tubular element 80. Body 251 may be any suitable length to traverse the length of tubular element 80 and have a sufficient amount of body 251 exposed outside tubular element 80 for robot system 1, through end-effectuator 30, or a surgeon to manipulate vertebral alignment tool 250 inside tubular element 80 for placement between vertebral body 600 and vertebral body 601, in disc space 602. Body 251 may be of any shape (i.e. square, rectangular, round, polyhedral, etc.) that may distract (i.e. separate vertebral body 600 and vertebral body 601) vertebral body 600 and vertebral body 601. Penetrating end 252 may be attached to body 251 at one end of body 251. Penetrating end 252 may comprise two individual projections which may have tapered ends that come to a point. Both projections may be of any desirable length or width so as to prevent interference with working channel 253. Working channel 253 may traverse the interior length of body 251. Working channel 253 may be of any shape (i.e. square, rectangular, round, polyhedral, etc.) desired by a surgeon. Furthermore, working channel 253 may allow for surgical tools to pass through body 251 and penetrating end 252 to enter the disc space for surgical operations.

FIGS. 15 and 16 illustrate body 251, which may be the width of tubular element 80 (i.e. cannula, dilator, or guide tube) used during the operation. As illustrated in FIG. 15, angled end 252 is positioned between two adjacent vertebral bodies 600, 601, which may not be prepared for surgical operations. As illustrated in FIG. 16, vertebral alignment tool 250 may be moved into disc space 602 between adjacent vertebral bodies 600, 601, distracting adjacent vertebral bodies 600, 601 for surgical operations. The pointed tip of penetrating end 252 penetrates through the soft tissue and annulus and into the disc space 602. The vertebral bodies 600, 601 may slide along the tapering of angled end 252, coming to rest upon body 251. With the vertebral body alignment tool 250, the surgeon may employ tools down working channel 253 of vertebral alignment tool 250 for surgical operations.

Figure 17:
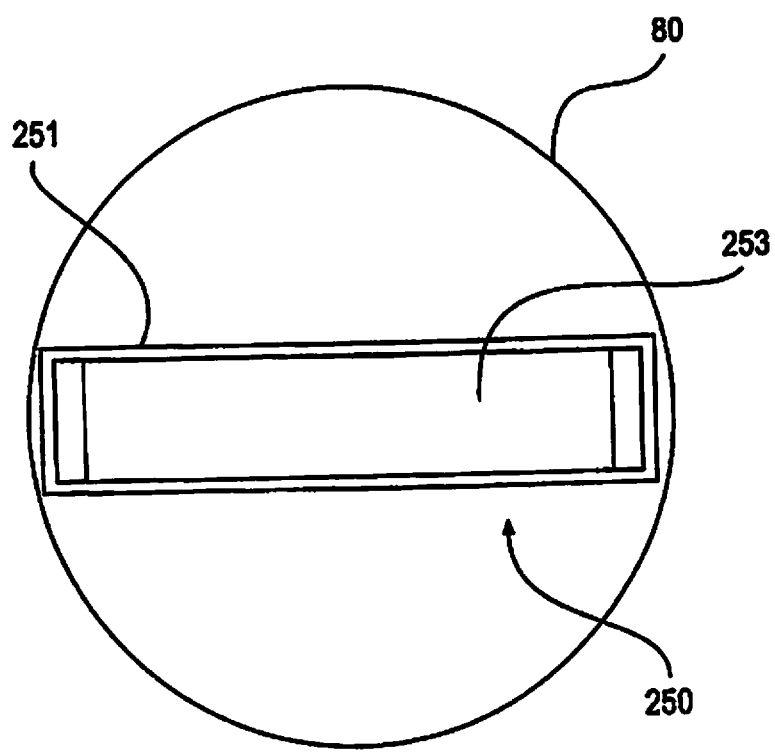
FIG. 17 illustrates a view looking down a tubular element with a vertebral alignment tool positioned inside the tubular element in accordance with one embodiment of the invention.

Illustrated in FIG. 17 is a view looking through working channel 253 of vertebral alignment tool 250 in accordance with some embodiments. The orientation of the vertebral bodies 600, 601 relative to tubular element 80 may be known, and therefore, it is possible to insert vertebral alignment tool 250 into the disc space in proper alignment with the vertebral bodies 600, 601 to allow entry between vertebral bodies 600, 601. A locking dial portal (not illustrated), may be used on the proximal end of end-effectuator 30, allowing robot system 1 to hold vertebral alignment tool 250 in place. The dial, (not illustrated), may move to a new radial position through end-effectuator 30 by control device 100. Through registration of the robot system 1 to CT image volume, as described earlier, and with additional spatial information from the position of the dial, exact orientation and position of the vertebral alignment tool 250 relative to the anatomy is known. Control device 100 may then insert or guide vertebral body tool 250 between two vertebral bodies 600, 601 using end-effectuator 30. Control device 100 may track the movement of the vertebral bodies 600, 601 and control the depth and movement of vertebral alignment tool 250 until the vertebral bodies 600, 601 may be in a parallel configuration. A drill assembly 500, with a depth stop (not illustrated), or other disc removal tool such as Kerrison or pituitary rongeurs may be safely inserted into the disc space 603, through working channel 253, between the vertebral bodies 600, 601 to remove disc material.

After the surgeon has completed the operation, control device 100 may remove vertebral alignment tool 250 using end-effectuator 30. Control device 100 may monitor the movement of the vertebral bodies and remove the vertebral alignment tool 250 in a manner that may not harm the vertebral bodies. Similarly, the surgeon may remove the end-effectuator 30 from vertebral alignment tool 250 and remove vertebral alignment tool 250 manually. This method may be employed to remove any cannula 121, dilators 200, or drill assembly safely from the patient 18, after surgery.

Figure 18:
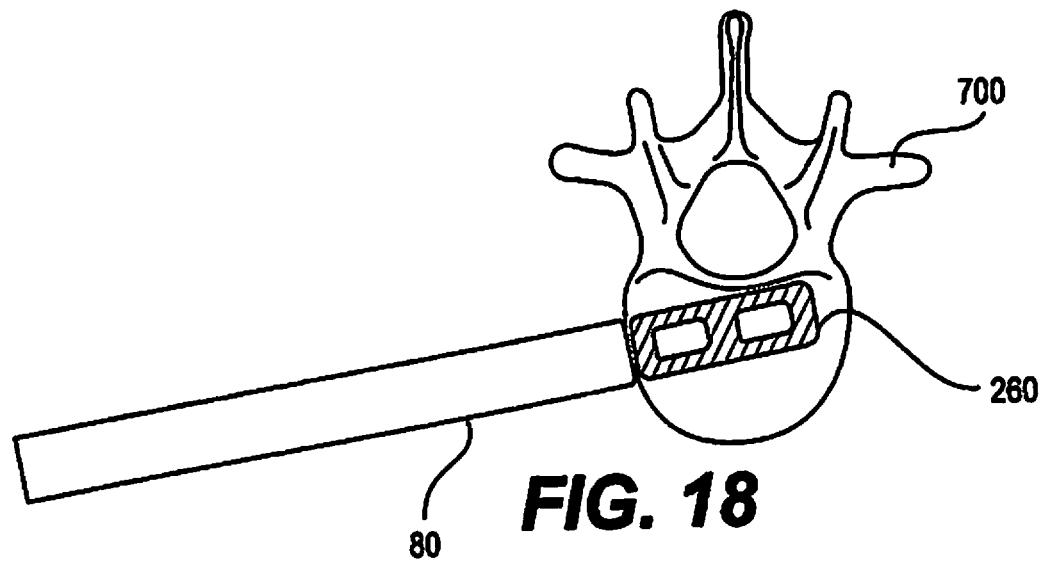
FIG. 18 illustrate an axial anatomical view of a vertebra with a tubular element and inserted interbody device in accordance with one embodiment of the invention.

Knowing the exact orientation of the disc space, by registration of patient 18 to robot system 1 (as discussed above), it may be possible to insert an interbody device 260 through tubular element 80, as illustrated in FIG. 18, during XLIF with much better knowledge and real-time feedback about the actual final positioning of the implant than is currently possible. As the interbody device 260 advances through tubular element 80 and into the disc space, a representation may be displayed on control device 100 through display means 29 with an axial view of the vertebral body 700, especially the disc space, and current location of the interbody device 260 overlaid, as illustrated in FIG. 18.

Another method for keeping track of the orientation of interbody device 260 is the dialable portal (not illustrated) as described above in the method of inserting vertebral alignment tool 250 using end-effectuator 30 of robot system 1. Such a portal would enable the user to control the orientation of the interbody device 260 during insertion and with feedback to control device 100 about the portal's angular orientation, either automatic through a sensor or manually entered by surgeon or technician, the orientation of the interbody device may be continuously monitored. An insertion tool (not illustrated) may have a sliding mechanism, which may be attached to end-effectuator 30, to orient the tool as is dictated by the portal.

Figure 19:
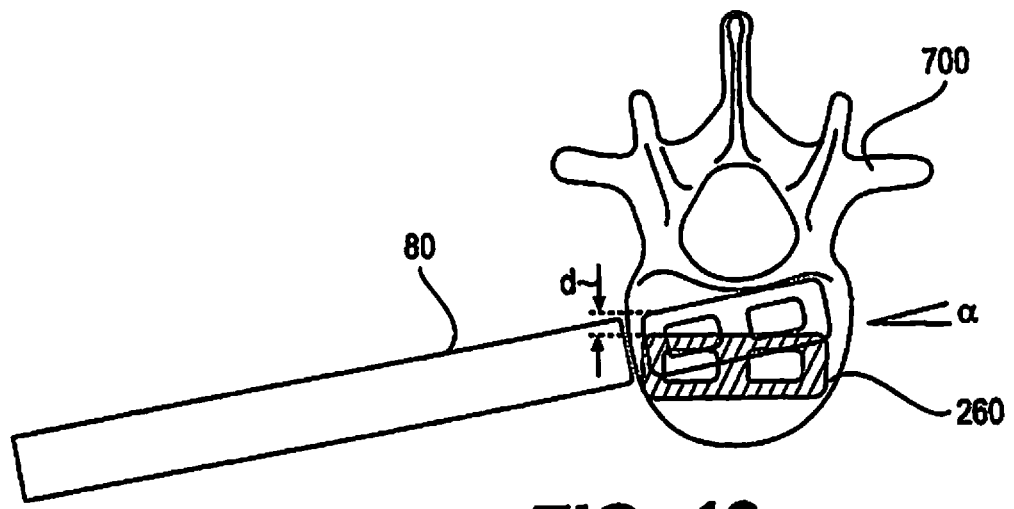
FIG. 19 illustrates an axial view of a vertebra with a tubular element and inserted interbody device with the distance and angle needed to correctly position the interbody device in accordance with one embodiment of the invention.

In FIG. 18, the interbody device 260 is intentionally illustrated malpositioned to clarify the degrees of freedom for which adjustment may be needed to fully seat interbody device 260 in the desired resting position. A surgeon advancing interbody device 260 from the lateral approach, predominantly moving interbody device 260 from a left to right position, may manipulate interbody device 260 as required to fully seat interbody device 260 in the desired resting position. Additionally, a means for manipulating predominantly the anterior-posterior position of interbody device 260 and a means of manipulating the rotational orientation of interbody device 260 in the plane may be required. One method for achieving the desired insertion is for the surgeon to dial in the necessary anteroposterior offset and the necessary rotation offset in robot system 1 integrated with tubular element 80, then to focus on advancing interbody device 260 through tubular element 80 until the desired depth of insertion is achieved. It may be necessary to displace interbody device 260 by the linear and rotational offset after advancing interbody device 260 and the insertion tool (not illustrated) far enough that interbody device 260 is clear of the distal end of tubular element 80 but before detaching interbody device 260 from the insertion tool. The desired final insertion depth may be controlled by an adjustable stop on the proximal end of tubular element 80 or by the user stopping when the user visually identifies interbody device 260 is far enough inserted on control device 100 through display means 29. Similarly, the angulation and linear offset of the interbody device 260 may be imposed after robot system 1 detects that at least some portion of interbody device 260 is clear of the distal end of tubular element 80 or after the user visually see the interbody device 260 is far enough inserted, on control device 100 through display means 29, that the displacement may not cause interbody device 260 to collide with tubular element 80. Detection of position and setting of robot system 1 may be automatically or manually controlled. That is, control device 100 may provide a surgeon with the anteroposterior distance "d" and the rotation angle "a", as illustrated in FIG. 19, that are required to reach the target after the surgeon has completed planning of the desired final location of interbody device 260 on control device 100 through display means 29. Alternately, control device 100 may automatically detect the required offsets and send a signal through robot system 1 to end-effectuator 30 to adjust to the appropriate offset positions.

Figure 20:
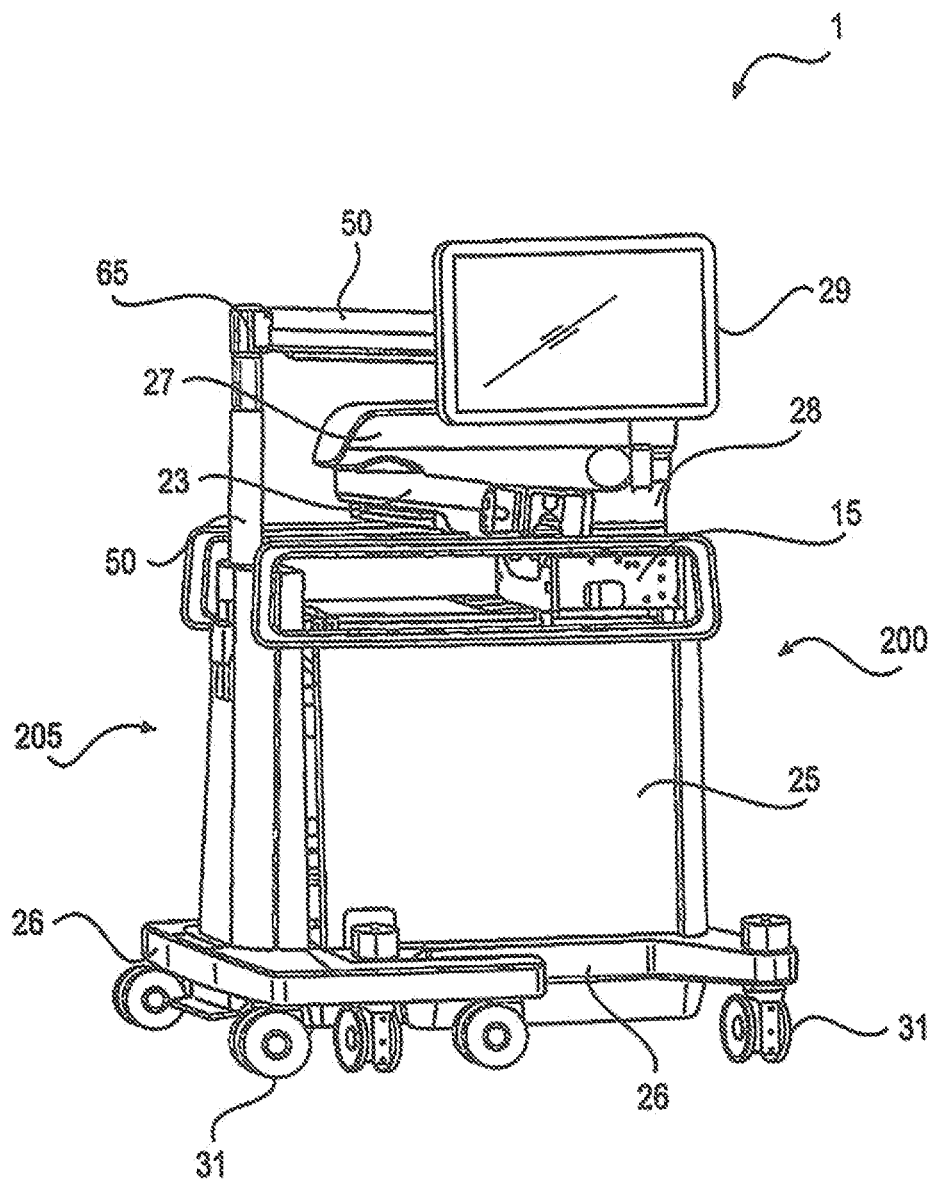
FIG. 20 illustrates a perspective view of a surgical robot according to an embodiment of the invention.
Figure 21:
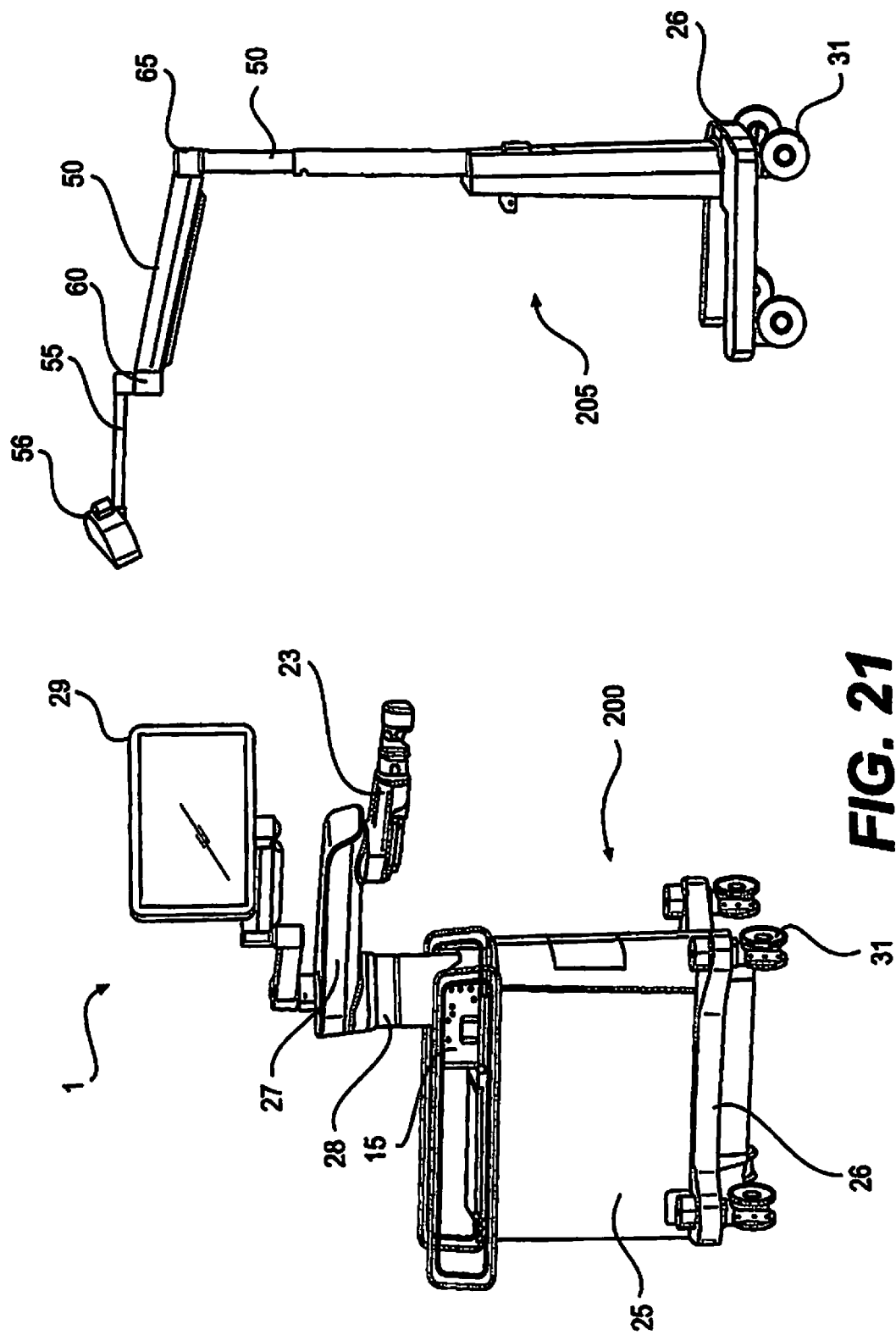
FIG. 21 illustrates a perspective view of a surgical robot separated in two structures according to an embodiment of the invention.

FIGS. 20 and 21 further illustrate embodiments of surgical robot system 1 that may be used for any surgical procedure described above. FIG. 20 illustrates surgical robot system 1 in a stowed position. In the stowed position, surgical robot system 1 may be maneuvered into any surgical room, storage room, or down any hallway. Robot system 1 may comprise of a base 25, a surgical robot 15, a support structure 28, a housing 27, a display means 29, and a robot arm 23. Robot system 1 may further comprise a plurality of arms 50, a joint 65, a joint 60, and a camera arm 55. Robot system 1 may be maneuvered using a plurality of wheels 31 which may attach to robot system 1 through a wheel base 26. Wheel base 26 may support robot system 1. As illustrated in FIG. 20, a first structure 200 and a second structure 205 may be attached to form robot system 1. First structure 200 may comprise of a base 25, a surgical robot 15, a support structure 28, a housing 27, a display means 29, and a robot arm 23. The second structure 205 may further comprise a plurality of arms 50, a joint 60, a joint 65, a camera 56, and camera arm 55.

FIG. 21 illustrates an embodiment of surgical robot system 1 in a deployed state, wherein structures 200 and 205 are separated from each other. First structure 200 may comprise a base 25, a surgical robot 15, a support structure 28, a housing 27, a display means 29, and a robot arm 23. Support structure 28 may support display means 29, housing 27, and robot arm 23. An end effectuator 30 (not pictured) may attach to robot arm 23 by any suitable means. End effectuator 30 may attach by any suitable means to any surgical tools described above (i.e. a cannula or drill assembly). Robot arm 23, end effectuator 30, and any attached surgical tools may operate according to any above described disclosure. Support structure 28 may rotate 360 degrees along the y-axis in relation to surgical robot 15. Robot arm 23 may further rotate or maneuver along the y-axis and x-axis, in relation to housing 27. Surgical robot 15 may move laterally along the y-axis in relation to base 25.

A second structure 205, illustrated in FIG. 21, may comprise a camera 56, a camera arm 55, a joint 60, a joint 65, a plurality of arms 50, a wheel base 26, and a plurality of wheels 31. Structure 205 may be positioned away from structure 200 by a surgeon in preparation for surgery. The surgeon my position structure 205 in any manner in relation to structure 200 to relay information from camera 56 to surgical robot 15. The second structure 205 may position camera 56 above a patient (not illustrated), or position camera 56 in any relation to the patient. Camera 56 may send information from second structure 205 to first structure 200. The information transmitted may be received by surgical robot 15 and transmitted to display means 29 for display.

Although the present invention and its advantages have been described in detail, it should be understood that various changes, substitutions and alterations may be made herein without departing from the spirit and scope of the invention as defined by the appended claims.

What is claimed is:

1. A method for removing bone with a robot system comprising:
   positioning along a desired trajectory an end effectuator to which a drill is adapted to be attached;
   retrieving a slice plane from a 3-D CT image scan volume, the retrieved slice plane being a two-dimensional slice lateral to the longitudinal axis of the drill attached to the end effectuator and being near the distal end of the drill; and
   controlling the drill to remove bone from the desired trajectory in the intersection of a defined perimeter and the slice plane;
   continuously retrieve a slice plane distally down the desired trajectory;
   for each retrieved slice plane, performing the following steps:
      repositioning the end effectuator such that the each retrieved slice plane is near the distal end of the drill; and
      controlling the drill to remove bone from the desired trajectory in the intersection of the defined perimeter and the each retrieved slice plane,
   wherein the each retrieved slice plane is a reformatted slice of the 3-D CT image scan volume, and
   wherein each retrieved slice plane is a two-dimensional slice perpendicular to the desired trajectory.

2. The method of claim 1, further comprising defining, by a user, a perimeter on a pathway through the anatomy.

3. The method of claim 1, further comprising displaying, on a display device, the each retrieved slice plane as the end effectuator is repositioned.

4. The method of claim 1, wherein the end effectuator includes a tube, further comprising inserting the drill through the end effectuator tube.

5. The method of claim 1, under the control of the robot system, automatically demarcating drilling area and non-drilling soft tissue area in the intersection of the defined perimeter and the each retrieved slice plane.

6. The method of claim 5, wherein the step of automatically demarcating includes demarcating using grayscale thresholding.

7. The method of claim 5, wherein the step of drilling includes controlling the drill to drill only in the drilling area under the control of the robot system.

8. The method of claim 1, under the control of the robot system, further comprising:
   automatically demarcating drilling area and non-drilling soft tissue area in the intersection of the defined perimeter and the each retrieved slice plane using gray scale thresholding; and
   wherein the step of drilling includes controlling the drill to drill only in the drilling area.

9. The method of claim 1, further comprising:
   identifying a critical structure to avoid in the slice plane; and
   placing a second perimeter around the identified critical structure within the first parameter.

10. The method of claim 9, controlling the drill to remove bone only within the second perimeter.

11. A method for inserting a tubular element into a patient with a robot system comprising:
    loading a 3-D computed tomography scan volume on to a control device of the robot system, the robot system further including a tubular element configured to receive a drill;
    programming a route for the tubular element to travel through the patient to a target anatomical location on a display, wherein the control device is configured to manipulate the tubular element; and
    controlling the tubular element with the robot system to guide the tubular element along the programmed route through the patient,
    wherein the control device calculates a two-dimensional slice lateral to the longitudinal axis of the drill and iteratively recalculates a slice plane distally down the programmed route and distal to the tubular element as the tubular element is advanced, and
    preparing a pathway for positioning of an implant,
    wherein each calculated slice plane is a two-dimensional slice perpendicular to the programmed route.

12. The method of claim 11, further comprising altering by a surgeon the programmed route while the robot system is moving the tubular element through the patient.

13. The method of claim 11, further comprising:
    continuously sensing neural activity through a neural sensing probe inserted into the tubular element; and
    automatically changing the programmed route based upon the neural activity sensed by the neural probe.

* * * * *